US006372207B1

(12) United States Patent
Tepper et al.

(10) Patent No.: US 6,372,207 B1
(45) Date of Patent: Apr. 16, 2002

(54) IFNAR2/IFN COMPLEX

(75) Inventors: Mark Tepper, Canton; Mark Cunningham, Waltham; David Sherris, Jamaica Plain; Nabil El Tayar, Milton; Sean McKenna, Ducksberry, all of MA (US)

(73) Assignee: Applied Research Systems ARS Holding N.V., Curacao (AN)

( * ) Notice: Subject to any disclaimer, the term of this patent is extended or adjusted under 35 U.S.C. 154(b) by 0 days.

(21) Appl. No.: 09/215,212

(22) Filed: Dec. 18, 1998

Related U.S. Application Data

(60) Provisional application No. 60/068,295, filed on Dec. 19, 1997.

(51) Int. Cl.[7] ........................ A61K 38/21; A61K 38/00; C12P 21/04; C07H 21/04

(52) U.S. Cl. .................... 424/85.4; 424/85.6; 424/85.7; 514/2; 435/69.51; 536/23.52

(58) Field of Search ............................ 514/2; 424/85.4, 424/85.6, 85.7; 530/350, 351; 435/69.51; 536/23.52

(56) References Cited

U.S. PATENT DOCUMENTS

| | | | | |
|---|---|---|---|---|
| 5,643,749 A | * | 7/1997 | Revel et al. ............... | 435/69.1 |
| 5,821,078 A | | 10/1998 | Novick et al. | |

FOREIGN PATENT DOCUMENTS

| | | |
|---|---|---|
| EP | 0588177 | 3/1994 |
| EP | 0679717 | 11/1995 |

OTHER PUBLICATIONS

Cohen, B., et al. (1995) Ligand–Induced Association of the Type I Interferon Receptor Components. *Mol. Cell. Biol.* 15(8): 4208–14.*

Novick, D., et al. (1995) Soluble and Membrane–Anchored Forms of the Human IFN–α/β Receptor. *J. Leukocyte Biol.* 57:712–18.*

Domanski, P. et al., "Cloning and Expression of a Long Form of the β Subunit of the Interferon αβ Receptor That is Required for Signaling," The Jourinal of Biological Chemistry 270–37:21606–21661 (1995).

Cutrone, E. C., "Contributions of cloned type I interferon receptor subunits to differential ligand binding," FEBS Letters 404:197–202 (1997).

* cited by examiner

*Primary Examiner*—Yvonne Eyler
*Assistant Examiner*—J. L. Andres
(74) *Attorney, Agent, or Firm*—Browdy and Neimark PLLC

(57) ABSTRACT

The in vivo effect of Type I interferon (IFN) can be prolonged by administering the interferon in the form of a complex with an IFN binding chain of the human interferon α/β receptor (IFNAR). Such a complex also improves the stability of the IFN and enhances the potency of the IFN. The complex may be a non-covalent complex or one in which the IFN and the IFNAR are bound by a covalent bond or a peptide. When bound by a peptide bond in the form of a fusion protein, the IFN may be separated from the IFNAR by means of a peptide linker. Such a fusion protein may be produced by recombinant DNA technology. Storing IFN in the form of such a complex improves the storage life of the IFN and permits storage under milder conditions than would otherwise be possible.

28 Claims, 13 Drawing Sheets

* PREINCUBATION FOR 3 HOURS @ 37°C WITH RATIO OF 2.5 ng IFNAR-2/IU IFN-β

PREINCUBATION OF IFN-β FOR 4 HOURS @ 37°C WITH 2.5 ng PROTEIN / IU IFN-β

FIG. 10

-29 Signal peptide 1 hIFNAR2
MLLSQNAFIV RSLNLVLMVY ISLVFGISYD SPDYTDESCT
FKISLRNFRS
22
ILSWELKNHS IVPTHYTLLY TIMSKPEDLK VVKNCANTTR
SFCDLTDEWR
72
STHEAYVTVL EGFSGNTTLF SCSHNFWLAI DMSFEPPEFE
IVGFTNHINV
122
MVKFPSIVEE ELQFDLSLVI EEQSEGIVKK HKPEIKGNMS
GNFTYIIDKL
172 210/211 GS linker
IPNTNYCVSV YLEHSDEQAV IKSPLKCTLL PPGQESEFSG
GGGSGGGGSM
221 hIFNβ
SYNLLGFLQR SSNFQCQKLL WQLNGRLEYC LKDRMNFDIP
EEIKQLQQFQ
272
KEDAALTIYE MLQNIFAIFR QDSSSTGWNE TIVENLLANV
YHQINHLKTV
322
LEEKLEKEDF TRGKLMSSLH LKRYYGRILH YLKAKEYSHC
AWTIVRVEIL
372 386
RNFYFINRLT GYLRN

Amino Acids: -29--1,signal sequence
+1-210,human IFNAR2
211-220,2x Gly4Ser linker
221-386,human IFNβ

SEQUENCE LISTING

```
<160> NUMBER OF SEQ ID NOS:  15

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:  Linker

<400> SEQUENCE: 1

Gly Gly Gly Gly Ser
  1               5


<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Factor
      Xa cleavage recognition signal

<400> SEQUENCE: 2

Ile Glu Glu Arg
  1


<210> SEQ ID NO 3
<211> LENGTH: 33
<212> TYPE: PRT
<213> ORGANISM: Artificial Sequence
<220> FEATURE:
<223> OTHER INFORMATION: Description of Artificial Sequence: C
      terminal human sIFNAR2 linked by linker to N terminal human
      IFNbeta

<400> SEQUENCE: 3

Glu Ser Glu Phe Ser Gly Gly Gly Gly Ser Gly Gly Gly Gly Ser Gly
  1               5                  10                  15

Gly Gly Gly Ser Gly Gly Gly Gly Ser Gly Gly Gly Gly Ser Met Ser
             20                  25                  30

Tyr


<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence: C
      terminal human sIFNAR2 linked by linker to N terminal human
      IFNbeta

<400> SEQUENCE: 4

Glu Ser Glu Phe Ser Gly Gly Gly Gly Ser Gly Gly Gly Gly Ser Gly
  1               5                  10                  15
Gly Gly Gly Ser Gly Gly Gly Gly Ser Met Ser Tyr
                     20                  25
```

-continued

<210> SEQ ID NO 5
<211> LENGTH: 23
<212> TYPE: PRT
<213> ORGANISM: Artificial Sequence
<220> FEATURE:
<223> OTHER INFORMATION: Description of Artificial Sequence: C terminal human sIFNAR2 linked by linker to N terminal human IFNbeta

<400> SEQUENCE: 5

```
Glu Ser Glu Phe Ser Gly Gly Gly Gly Ser Gly Gly Gly Gly Ser Gly
  1               5                  10                  15

Gly Gly Gly Ser Met Ser Tyr
             20
```

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: C terminal human sIFNAR2 linked by linker to N terminal human IFNbeta

<400> SEQUENCE: 6

```
Glu Ser Glu Phe Ser Gly Gly Gly Gly Ser Gly Gly Gly Gly Ser Met
  1               5                  10                  15

Ser Tyr
```

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: C terminal human sIFNAR2 linked by linker to N terminal human IFNbeta

<400> SEQUENCE: 7

```
Glu Ser Glu Phe Ser Gly Gly Gly Gly Ser Met Ser Tyr
  1               5                  10
```

<210> SEQ ID NO 8
<211> LENGTH: 36
<212> TYPE: PRT
<213> ORGANISM: Artificial Sequence
<220> FEATURE:
<223> OTHER INFORMATION: Description of Artificial Sequence: C terminal human sIFNAR2 linked by hCG-CTP linker to N terminal human IFNbeta

<400> SEQUENCE: 8

```
Glu Ser Glu Phe Ser Ser Ser Ser Ser Lys Ala Pro Pro Pro Ser Leu
  1               5                  10                  15

Pro Ser Pro Ser Arg Leu Pro Gly Pro Ser Asp Thr Pro Ile Leu Pro
             20                  25                  30

Gln Met Ser Tyr
         35
```

<210> SEQ ID NO 9
<211> LENGTH: 23
<212> TYPE: PRT
<213> ORGANISM: Artificial Sequence
<220> FEATURE:
<223> OTHER INFORMATION: Description of Artificial Sequence: C terminal human sIFNAR2 linked by linker to N terminal human IFNbeta -continued

<400> SEQUENCE: 9

Glu Ser Glu Phe Ser Glu Phe Met Glu Phe Met Glu Phe Met Glu Phe
1 5 10 15

Met Glu Phe Met Met Ser Tyr
20

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: C terminal human sIFNAR2 linked by linker to N terminal human IFNbeta

<400> SEQUENCE: 10

Glu Ser Glu Phe Ser Glu Phe Met Glu Phe Met Glu Phe Met Glu Phe
1 5 10 15

Met Met Ser Tyr
20

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: C terminal human sIFNAR2 linked by linker to N terminal human IFNbeta

<400> SEQUENCE: 11

Glu Ser Glu Phe Ser Glu Phe Met Glu Phe Met Glu Phe Met Met Ser
1 5 10 15

Tyr

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: C terminal human sIFNAR2 linked by linker to N terminal human IFNbeta

<400> SEQUENCE: 12

Glu Ser Glu Phe Ser Glu Phe Gly Ala Gly Leu Val Leu Gly Gly Gln
1 5 10 15

Phe Met Met Ser Tyr
20

<210> SEQ ID NO 13
<211> LENGTH: 34
<212> TYPE: PRT
<213> ORGANISM: Artificial Sequence
<220> FEATURE:
<223> OTHER INFORMATION: Description of Artificial Sequence: C terminal human sIFNAR2 linked by linker to N terminal human IFNbeta

<400> SEQUENCE: 13

Glu Ser Glu Phe Ser Glu Phe Gly Ala Gly Leu Val Leu Gly Gly Gln
1 5 10 15

-continued

```
Phe Met Glu Phe Gly Ala Gly Leu Val Leu Gly Gly Gln Phe Met Met
            20                  25                  30

Ser Tyr


<210> SEQ ID NO 14
<211> LENGTH: 415
<212> TYPE: PRT
<213> ORGANISM: Artificial Sequence
<220> FEATURE:
<223> OTHER INFORMATION: Description of Artificial Sequence:
      Human sIFNAR2 linked by linker to human IFNbeta
<223> OTHER INFORMATION: Residues 1-29, signal sequence; 30-239,
      human IFNAR2; 240-249, 2X Gly4Ser linker; 250-415, human IFNbeta

<400> SEQUENCE: 14

Met Leu Leu Ser Gln Asn Ala Phe Ile Val Arg Ser Leu Asn Leu Val
  1               5                  10                  15

Leu Met Val Tyr Ile Ser Leu Val Phe Gly Ile Ser Tyr Asp Ser Pro
            20                  25                  30

Asp Tyr Thr Asp Glu Ser Cys Thr Phe Lys Ile Ser Leu Arg Asn Phe
        35                  40                  45

Arg Ser Ile Leu Ser Trp Glu Leu Lys Asn His Ser Ile Val Pro Thr
     50                  55                  60

His Tyr Thr Leu Leu Tyr Thr Ile Met Ser Lys Pro Glu Asp Leu Lys
 65                  70                  75                  80

Val Val Lys Asn Cys Ala Asn Thr Thr Arg Ser Phe Cys Asp Leu Thr
                 85                  90                  95

Asp Glu Trp Arg Ser Thr His Glu Ala Tyr Val Thr Val Leu Glu Gly
            100                 105                 110

Phe Ser Gly Asn Thr Thr Leu Phe Ser Cys Ser His Asn Phe Trp Leu
        115                 120                 125

Ala Ile Asp Met Ser Phe Glu Pro Pro Glu Phe Glu Ile Val Gly Phe
    130                 135                 140

Thr Asn His Ile Asn Val Met Val Lys Phe Pro Ser Ile Val Glu Glu
145                 150                 155                 160

Glu Leu Gln Phe Asp Leu Ser Leu Val Ile Glu Glu Gln Ser Glu Gly
                165                 170                 175

Ile Val Lys Lys His Lys Pro Glu Ile Lys Gly Asn Met Ser Gly Asn
            180                 185                 190

Phe Thr Tyr Ile Ile Asp Lys Leu Ile Pro Asn Thr Asn Tyr Cys Val
        195                 200                 205

Ser Val Tyr Leu Glu His Ser Asp Glu Gln Ala Val Ile Lys Ser Pro
    210                 215                 220

Leu Lys Cys Thr Leu Leu Pro Pro Gly Gln Glu Ser Glu Phe Ser Gly
225                 230                 235                 240

Gly Gly Gly Ser Gly Gly Gly Gly Ser Met Ser Tyr Asn Leu Leu Gly
                245                 250                 255

Phe Leu Gln Arg Ser Ser Asn Phe Gln Cys Gln Lys Leu Leu Trp Gln
            260                 265                 270

Leu Asn Gly Arg Leu Glu Tyr Cys Leu Lys Asp Arg Met Asn Phe Asp
        275                 280                 285

Ile Pro Glu Glu Ile Lys Gln Leu Gln Gln Phe Gln Lys Glu Asp Ala
    290                 295                 300

Ala Leu Thr Ile Tyr Glu Met Leu Gln Asn Ile Phe Ala Ile Phe Arg
305                 310                 315                 320
```

-continued

```
Gln Asp Ser Ser Ser Thr Gly Trp Asn Glu Thr Ile Val Glu Asn Leu
                325                 330                 335

Leu Ala Asn Val Tyr His Gln Ile Asn His Leu Lys Thr Val Leu Glu
            340                 345                 350

Glu Lys Leu Glu Lys Glu Asp Phe Thr Arg Gly Lys Leu Met Ser Ser
        355                 360                 365

Leu His Leu Lys Arg Tyr Tyr Gly Arg Ile Leu His Tyr Leu Lys Ala
    370                 375                 380

Lys Glu Tyr Ser His Cys Ala Trp Thr Ile Val Arg Val Glu Ile Leu
385                 390                 395                 400

Arg Asn Phe Tyr Phe Ile Asn Arg Leu Thr Gly Tyr Leu Arg Asn
                405                 410                 415


<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: C
      terminal human sIFNAR2 directly connected to N terminal human
      IFNbeta

<400> SEQUENCE: 15

Glu Ser Glu Phe Ser Met Ser Tyr
  1               5
```

IFNAR2/IFN COMPLEX

CROSS-REFERENCE TO RELATED APPLICATIONS

The present application claims priority from U.S. provisional application Ser. No. 60/068,295, filed Dec. 19, 1997, the entire contents of which are hereby incorporated by reference.

FIELD OF INVENTION

The present invention relates to a Type I interferon complex, composed of the polypeptide sequence of the human interferon α/β receptor (IFNAR2) extracellular domain and a Type I interferon (IFNα, IFNβ, and IFNω). Such a complex improves the stability, enhances the potency, and prolongs the pharmacokinetics in vivo of free IFN for anti-viral, anti-cancer and immune modulating activity. More particularly, the complex is a fusion protein, or a covalent complex, or a non-covalent complex containing the polypeptide sequence of the entire extracellular domain of IFNAR2, or any interferon-binding subfraction thereof, complexed to a Type I interferon (IFNα, IFNβ, IFNω), or any biologically active subfraction thereof.

BACKGROUND OF INVENTION

Interferons are classified either as the leukocyte and fibroblast derived Type I interferons, or as the mitogen induced or "immune" Type II interferons (Pestka et al, 1987). Through analysis of sequence identities and common biological activities, Type I interferons include interferon alpha (IFNα), interferon beta (IFNβ) and interferon omega (IFNω), while Type II interferon includes interferon gamma (IFNγ). The IFNα, IFNβ and IFNω genes are clustered on the short arm of chromosome 9 (Lengyl, 1982). There are at least 25 non-allelic IFNα genes, 6 non-allelic IFNω genes and a single IFNβ gene. All are believed to have evolved from a single common ancestral gene. Within species, IFNα genes share at least 80% sequence identity with each other. The IFNβ gene shares approximately 50% sequence identity with IFNα; and the IFNω gene shares 70% homology with IFNα (Weissman et al, 1986; Dron et al, 1992). IFNα has a molecular weight range of 17–23 kDa (165–166 amino acids), IFNβ, ~23 kDa (166 amino acids) and IFNω, ~24 kDa (172 amino acids).

Type I interferons are pleiotropic cytokines having activity in host defense against viral and parasitic infections, as anti-cancer cytokines and as immune modulators (Baron et al, 1994; Baron et al, 1991). Type I interferon physiological responses include anti-proliferative activity on normal and transformed cells; stimulation of cytotoxic activity in lymphocytes, natural killer cells and phagocytic cells; modulation of cellular differentiation; stimulation of expression of class I MHC antigens; inhibition of class II MHC; and modulation of a variety of cell surface receptors. Under normal physiological conditions, IFNα and IFNβ (IFNα/β) are secreted constitutively by most human cells at low levels with expression being up-regulated by addition of a variety of inducers, including infectious agents (viruses, bacteria, mycoplasma and protozoa), dsRNA, and cytokines (M-CSF, IL-1α, IL-2, TNFα). The actions of Type I interferon in vivo can be monitored using the surrogate markers, neopterin, 2', 5' oligoadenylate synthetase, and β2 microglobulin (Alam et al, 1997; Fierlbeck et al, 1996; Salmon et al, 1996).

Type I interferons IFNα/β/ω) act through a cell surface receptor complex to induce specific biologic effects, such as anti-viral, anti-tumor, and immune modulatory activity. The Type I IFN receptor (IFNAR) is a hetero-multimeric receptor complex composed of at least two different polypeptide chains (Colamonici et al, 1992; Colamonici et al, 1993; Platanias et al, 1993). The genes for these chains are found on chromosome 21, and their proteins are expressed on the surface of most cells (Tan et al, 1973). The receptor chains were originally designated alpha and beta because of their ability to be recognized by the monoclonal antibodies IFNαR3 and IFNaRβ1, respectively. Most recently, these have been renamed IFNAR1 for the alpha subunit and IFNAR2 for the beta subunit. In most cells, IFNAR1 (alpha chain, Uze subunit) (Uze et al, 1990) has a molecular weight of 100–130 kDa, while IFNAR2 (beta chain, $B_L$, IFNα/βR) has a molecular weight of 100 kDa. In certain cell types (monocytic cell lines and normal bone marrow cells) an alternate receptor complex has been identified, where the IFNAR2 subunit ($\beta_S$) is expressed as a truncated receptor with a molecular weight of 51 kDa. The IFNAR1 and IFNAR2 $\beta_S$ and $\beta_L$ subunits have been cloned (Novick et al, 1994; Domanski et al, 1995). The IFNAR2 $\beta_S$ and $\beta_L$ subunits have identical extracellular and transmembrane domains; however, in the cytoplasmic domain they only share identity in the first 15 amino acids. The IFNAR2 subunit alone is able to bind IFNα/β, while the IFNAR1 subunit is unable to bind IFNα/β. When the human IFNAR1 receptor subunit alone was transfected into murine L-929 fibroblasts, no human IFNαs except IFNα8/IFNαB were able to bind to the cells (Uze et al, 1990). The human IFNAR2 subunit, transfected into L cells in the absence of the human IFNAR1 subunit, bind human IFNα2, binding with a Kd of approximately 0.45 nM. When human IFNAR2 subunits were transfected in the presence of the human IFNAR1 subunit, high affinity binding could be shown with a Kd of 0.026–0.114 nM (Novick et al, 1994; Domanski et al, 1995). It is estimated that from 500–20,000 high affinity and 2,000–100,000 low affinity IFN binding sites exist on most cells. Although the IFNAR1/2 complex ($\alpha/\beta_s$ or $\alpha/\beta_L$) subunits bind IFNα with high affinity, only the $\alpha/\beta_L$ pair appears to be a functional signaling receptor.

Transfection of the IFNAR1 and the IFNAR2 $\beta_L$ subunits into mouse L-929 cells, followed by incubation with IFNα2, induces an anti-viral state, initiates intracellular protein phosphorylation, and causes the activation of intracellular kinases (Jak1 and Tyk2) and transcription factors (STAT 1, 2, and 3) (Novick et al, 1994; Domanski et al, 1995). In a corresponding experiment, transfection of the IFNAR2 $\beta_S$ subunit was unable to initiate a similar response. Thus, the IFNAR2 $\beta_L$ subunit is required for functional activity (anti-viral response) with maximal induction occurring in association with the IFNAR1 subunit.

In addition to membrane bound cell surface IFNAR forms, a soluble IFNAR has been identified in both human urine and serum (Novick et al, 1994; Novick et al, 1995; Novick et al, 1992; Lutfalla et al, 1995). The soluble IFNAR isolated from serum has an apparent molecular weight of 55 kDa on SDS-PAGE, while the soluble IFNAR from urine has an apparent molecular weight of 40–45 kDa (p40). Transcripts for the soluble p40 IFNAR2 are present at the mRNA level and encompass almost the entire extracellular domain of the IFNAR2 subunit with two new amino acids at the carboxy terminal end. There are five potential glycosylation sites on the soluble IFNAR2 receptor. The soluble p40 IFNAR2 has been shown to bind IFNα2 and IFNβ and to inhibit in vitro the anti-viral activity of a mixture of IFNα species ("leukocyte IFN") and individual Type I IFNs (Novick et al, 1995). A recombinant IFNAR2 subunit Ig fusion protein was shown to inhibit the binding of a variety of Type I IFN species (IFNαA, IFNαB, IFNαD, IFNβ, IFNα Con1 and IFNω) to Daudi cells and $\alpha/\beta_S$ subunit double transfected COS cells.

Type I IFN signaling pathways have recently been identified (Platanias et al, 1996; Yan et al, 1996; Qureshi et al, 1996; Duncan et al, 1996; Sharf et al, 1995; Yang et al, 1996). Initial events leading to signaling are thought to occur by the binding of IFNα/β/ω to the IFNAR2 subunit, followed by the IFNAR1 subunit associating to form an IFNAR1/2 complex (Platanias et al, 1994). The binding of IFNα/β/ω to the IFNAR1/2 complex results in the activation of two Janus kinases (Jak1 and Tyk2) which are believed to phosphorylate specific tyrosines on the IFNAR1 and IFNAR2 subunits. Once these subunits are phosphorylated, STAT molecules (STAT 1, 2 and 3) are phosphorylated, which results in dimerization of STAT transcription complexes followed by nuclear localization of the transcription complex and the activation of specific IFN inducible genes.

The pharmacokinetics and pharmacodynamics of Type I IFNs have been assessed in humans (Alan et al, 1997; Fierlbeck et al, 1996; Salmon et al, 1996). The clearance of IFNβ is fairly rapid with the bioavailability of IFNβ lower than expected for most cytokines. Although the pharmacodynamics of IFNβ have been assessed in humans, no clear correlation has been established between the bioavailability of IFNβ and clinical efficacy. In normal healthy human volunteers, administration of a single intravenous (iv) bolus dose (6 MIU) of recombinant CHO derived IFNβ resulted in a rapid distribution phase of 5 minutes and a terminal half-life of ~5 hours (Alam et al, 1997). Following subcutaneous (sc) or intramuscular (im) administration of IFNβ, serum levels are flat with only ~15% of the dose systemically available. The pharmacodynamics of IFNβ following iv, im or sc administration (as measured by changes in 2'5'-oligoadenylate synthetase (2',5'-AS) activity in PBMCs) were elevated within the first 24 hours and slowly decreased to baseline levels over the next 4 days. The magnitude and duration of the biologic effect was the same regardless of the route of administration.

The pharmacokinetics (PK) and pharmacodynamics (PD) of IFNβ manufactured by two different companies (REBIF®-Serono and AVONEX®-Biogen) has been examined following the im injection of a single dose of 6 MIU of recombinant IFNβ (Salmon, 1996). Serum concentration of IFNβ and the IFNβ surrogate marker, neopterin, were monitored over time. Both IFNβ preparations exhibited similar PK profiles with peak serum levels of IFNβ achieved by ~12–15 hours, although REBIF® gave lower maximum levels. The IFNβ levels remained elevated for both REBIF® and AVONEX® for at least the first 36 hours post im injection and then dropped to slightly above baseline by 48 hours. Levels of neopterin exhibited a very similar profile between REBIF® and AVONEX® with maximal neopterin levels achieved at ~44–50 hours post-injection, remaining elevated until 72 hours post-injection and then dropping to baseline gradually by 144 hours.

A multiple dose pharmacodynamic study of IFNβ has been conducted in human melanoma patients (Fierlbeck et al, 1996) with IFNβ being administrated by sc route, three times per week at 3 MIU/dose over a six-month period. The pharmacodynamic markers, 2', 5'-AS synthetase, β2-microglobulin, neopterin, and NK cell activation peaked by the second injection (day 4) and dropped off by 28 days, remaining only slightly elevated out to six months.

In summary, the clearance of Type I interferons in humans is rapid. A long-acting interferon preparation would likely result in an improvement in clinical benefit.

SUMMARY OF THE INVENTION

It has now been found that a Type I interferon complex, composed of soluble IFNAR complexed with Type I interferons (IFN), exhibits improved stability, enhanced potency, and elongated pharmacokinetics in vivo compared with free IFN for anti-viral, anti-cancer and immune modulating activity.

The present invention thus provides a Type I interferon (IFN) complex, composed of the polypeptide sequence of a human interferon α/β receptor (IFNAR) subunit extracellular domain and Type I interferons, which exhibits improved stability, enhanced potency, and/or prolonged pharmacokinetics in vivo compared to free IFN for anti-viral, anti-cancer and immune modulating activity. Preferably, the complex is of the IFNAR2 subunit extracellular domain with any Type I interferon or the IFNAR1 subunit with IFNα.

More specifically, the complex is a fusion protein, or a covalent complex, or a non-covalent complex containing the polypeptide sequence of the entire extracellular domain of IFNAR, preferably IFNAR2, or any interferon-binding subfraction thereof, complexed to IFNα or IFNβ or IFNω, or any biologically active subfraction thereof.

IFNAR is intended to comprehend any of the known extracellular IFNAR receptors as defined above, as well as any active fragments thereof. IFNAR can be optionally fused to another protein, for example, an immunoglobulin such as IgG. IFN, IFNα, IFNβ, and IFNω are intended as one of the more than 20 Type I interferons identified to date, or any other Type I interferon identified in the future.

In one embodiment of the present invention, the complex is composed of IFNα or IFNβ, covalently linked to IFNAR2 via chemical linkage.

A further embodiment comprises a complex composed of IFNα or IFNβ, non-covalently complexed to IFNAR2. This further embodiment also includes a composition containing a Type I IFN and IFNAR2 in any ratio. A formulation of Type I IFN with an excess of IFNAR2 as defined above is also included in the definition of "complex" of the present application. The two components may also be administered separately so as to form the complex in vivo. Thus, in a further embodiment, the complex is a mixture of IFNAR2 and IFN, obtained by simultaneous or subsequent co-administration of IFNα or IFNβ and soluble IFNAR2. Furthermore, the IFNAR can be administered without any concomitant administration of IFN, so that the complex may be formed in vivo with endogenous circulating IFN, thereby potentiating the effects of the endogenous IFN.

As a particular embodiment, the complex is composed of IFNα or IFNβ or IFNω fused to IFNAR2 as a recombinant fusion protein, where the IFN and the IFNAR2 moieties are optionally fused via a flexible peptide linker molecule. This peptide linker may or may not be cleavable in vivo.

The invention further relates to DNA encoding such fusion proteins, vectors containing such DNA, host cells transformed with such vectors in such a manner as to express the fusion proteins and methods of production of such fusion proteins by culturing such host cells and isolating the fusion proteins expressed thereby.

A further aspect of the present invention are the methods of use of the complexes of the present invention for prolonging the in vivo effect of IFN, which is useful in the treatment of any disease or condition which is treatable by IFN.

Another aspect of the present invention relates to the use of IFNAR as a stabilizer in formulations of IFN. Free IFNβ has a tendency to oligomerize. This is prevented once it is complexed to IFNAR, particularly IFNAR2. Present day formulations of recombinant IFNβ must have an acidic pH, which may cause some localized irritation when administered. Non-acidic compositions can be formulated if IFNAR is used as a stabilizer.

BRIEF DESCRIPTION OF THE DRAWINGS

The present invention will be better understood in conjunction with the following drawings, in which:

FIG. 10 shows the amino acid sequence of the n=2 IFNAR2/IFNβ fusion protein (SEQ ID NO:14). The $(GGGGS)_2$ (residues 240–249 of SEQ ID NO:14) linker is underlined.

DETAILED DESCRIPTION OF PREFERRED EMBODIMENTS

Figure 1:
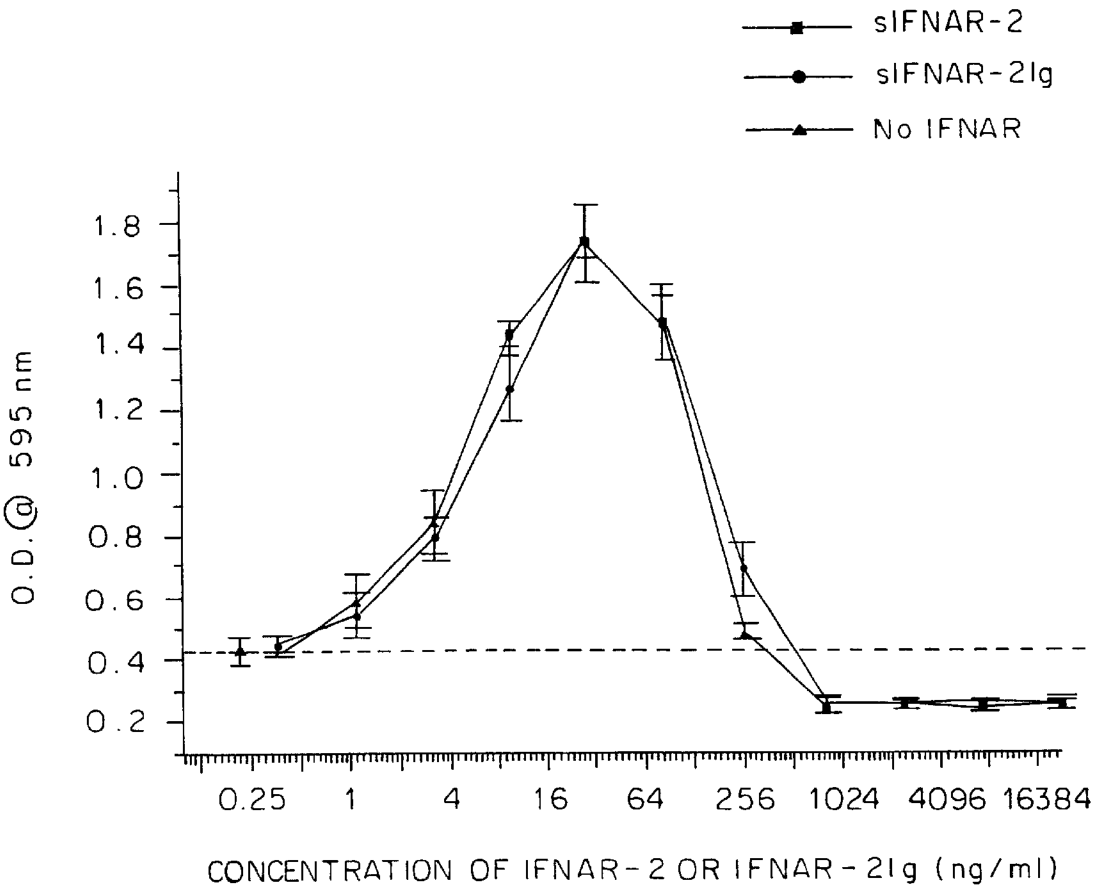
FIG. 1 is a graph showing dose-dependent anti-viral activity of sIFNAR2 or IFNAR2Ig (composed of the extracellular domain of hIFNAR2 fused to human IgG1 hinge, CH2 and CH3 domains) in the presence of IFNβ.

The IFNAR/IFN complex of the present invention and the enabling technology required to produce this complex is described in detail hereinbelow. For most of the results, IFNβ has been chosen as a non-limiting example.

Fusion Protein. The C-terminal end of IFNAR2, or any interferon-binding subsequence thereof, has been fused to the N-terminal end of IFNβ, or biologically active fragments thereof, as this requires the shortest distance to be bridged between the two molecules. The reverse constructs can also be prepared, where the C-terminal end of IFNβ, or fragments thereof, are fused to the N-terminal end of IFNAR2, or subsequences thereof.

From molecular models of the IFNAR2/IFNβ complex, the estimated distance between the constrained C-terminal extracellular domain of IFNAR2 and the N-terminal of IFNβ in the active complex model is ~80 Angstroms. In order to engineer an IFNAR2/IFNβ complex which allows the active complex to be maintained, a flexible peptide linker, for example, Gly-Gly-Gly-Gly-Ser (GGGGS) (SEQ ID NO:1) repeats, may be employed. Alternatively, the linker may be flexible and a target for proteolytic cleavage by serum, membrane bound, and/or cellular proteases. As example for a serum protease cleavage site the engineered IFNAR2/IFNβ complex fusion may have a Factor Xa cleavage site. Factor Xa cleaves prothrombin at two locations Arg273 and Arg322, and it has a tetrapeptide recognition signal Ile-Glu-Glu-Arg (SEQ ID NO:2) (Nagai et al, 1984). Factor Xa itself is generated from both intrinsic and extrinsic pathways by a variety of activators, including tissue factor, which is released by vascular endothelial cells, macrophages and neutrophils.

Factor Xa can act on a sIFNAR2/IFN fusion protein containing a Factor Xa recognition sequence in the linker domain and release the IFNAR2/IFN complex such that the complex can function as a non-covalent complex.

Alternatively, the IFNAR2/IFNβ complex fusion may have a cell membrane protease (e.g., hepsin) cleavage site. Hepsin is a 51 kDa membrane bound serine protease zymogen expressed in high levels in liver tissue but is also found in kidney, pancreas, lung, thyroid, pituitary and testis.

One sequence known to be cleaved by hepsin is the Arg152-Ile153 peptide bond in Factor VII. Hepsin has been implicated in the formation of thrombin on tumor cells (Kazam et al, 1995).

Hepsin can act on a sIFNAR2/IFN fusion protein containing a hepsin recognition sequence in the linker domain and release the IFNAR2/IFN complex such that the complex can function in a non-covalent fashion.

Alternatively, the IFNAR2/IFNα fusion complex may have an intracellular protease cleavage site. A variety of proteases are released by necrosing and apoptosing cells. Included in these are caspases (Interleukin 1 beta-converting enzyme-like proteases), metallo proteinases, lysosomal proteases (e.g., cathepsin B) and elastase. Elastase is released by granulocytes during disease states (e.g., sepsis) and has a broad specificity regarding amino acid cleavage sequence, akin to that of trypsin (Ertel et al, 1994; Szilagyi et al, 1995).

Intracellular proteases can act on a sIFNAR2/IFN fusion protein containing an intracellular protease recognition sequence in the linker domain and release the IFNAR2/IFN complex such that the complex can function as a non-covalent complex.

Several examples of fusion protein constructs in which the C-terminal of sIFNAR2 (P40-ESEFS) (residues 1–5 of SEQ ID No. 3) is linked to the N-terminal of IFNβ (MSY) via flexible linkers have, in fact, been prepared. Examples of peptide linkers are as follows: ESEFS(GGGGS)$_n$MSY, where n=5 (SEQ ID NO:3), 4 (SEQ ID NO:4), 3 (SEQ ID NO:5), 2 (SEQ ID NO:6), or 1 (SEQ ID NO:7); ESEFS (hCG-CTP)MSY where hCG-CTP= SSSSKAPPPSLPSPSRLPGPSDTPILPQ (SEQ ID NO:8); ESEFS(EFM)$_n$MSY, where n=5 (SEQ ID NO:9), 4 (SEQ ID NO:10), or 3 (SEQ ID NO:11); ESEFS (EFGAGLVLGGQFM)$_n$MSY where n=1 (SEQ ID NO:12), or 2 (SEQ ID NO:13) and any other suitable linker which spans the distance between the IFNAR2 binding site and IFNβ in the complex model and which do not form an immunogenic epitope between the interferon and receptor moieties. Preferably, these linkers are up to about 30 amino acids in length.

Covalent Complex. One example of generating chemical crosslinked molecules is to site-specifically modify the IFNAR2 by reacting a biodegradable linker, such as polyethylene glycol (PEG), with cysteines present or engineered into IFNAR2 using either an amino acid substitution, such as. $Ser_{210}$ to Cys or $Asn_{89}$ to Cys, (site-directed mutagenesis). The following constructs could be engineered: IFNAR(S210C)-PEGn-IFNβ(Cys17) where n=2000, 5000 or 10,000 Daltons or IFNAR(N89C)-PEGn-IFNβ(Cys17).

Formation of covalent disulfide bonds between Cys of the two different (optionally-engineered) moieties is also within the scope of the present invention.

Non-Covalent Complex. Human IFNAR2 is complexed with IFNβ under conditions which maximize the generation of the active complex. In vitro, an optimum ratio of 2.5 ng of IFNAR2 to 1 international unit (IU) of IFNβ is required to yield a maximally active complex, as reported in the examples. The optimum ratio of IFNAR2 to IFNβ which maximizes the generation of the active complex for in vivo activity is currently being determined, although it appears that the optimum ratio will be dependent on the concentration of IFNβ. Thus, for example, the optimum ratio of IFNAR2:IFNβ in the enhancement of anti-tumor activity at a concentration of $2\times10^4$ IU/mouse/day IFNβ was 2.5 ng IFNAR2 per pg IFNβ, while at a concentration of $5\times10^4$ IU/mouse/day IFNβ, 0.3 ng IFNAR2 per pg IFNβ was optimum. The same ratio as used to maximize the generation of the active complex in vitro resulted in elongated pharmacokinetics of the IFN in vivo.

Preferably, IFNAR2 and IFNβ used to generate the complex are recombinant molecules. In in vitro anti-viral assays, the interferon/receptor complex exhibited enhanced activity when compared to the activity of IFNβ alone. A constant concentration of IFNβ was mixed with varying concentrations of recombinant sIFNAR2, and this mixture (IFNAR2/IFN complex) was added to WISH cells (human amniotic cells). These WISH cells were then challenged with vesicular stomatitis virus (VSV), and the anti-viral activity of IFN monitored as the degree of cell survival following 48-hour incubation. In each of the experiments, the addition of IFNAR2 to a constant amount of IFNβ resulted in a dose-dependent increase in cell survival upon challenge with VSV at a optimum ratio of IFNAR2 to IFN. These results prove that a complex of IFNAR2 and IFNβ exhibits enhanced activity compared to free IFNβ in an anti-viral assay. The practical implications of this are that the IFNAR2/IFNβ complex has greater potency and enhanced activity compared to free IFN for a variety of therapeutic indications in which IFN by itself is active. These indications include those in which free IFNs have shown some therapeutic activity, such as anti-viral, anti-cancer and immune modulatory activity. It is expected that the IFNAR2/IFN complex, by virtue of its greater potency, enhanced activity and/or improved pharmacokinetics (i.e. half-life), will be more efficacious in treating viral, oncologic and immune disorders.

When administered in vivo, the interferon receptor complex enhances the bioavailability, pharmacokinetics, and/or pharmacodynamics of the IFN, thus augmenting the anti-viral, anti-cancer and immune modulating properties of the IFN.

The enhanced bioavailability of IFN mediated by the complex can be gained by either pre-formation of an IFN/IFNAR non-covalent complex, co-administration of free IFN with IFNAR, via administration of the IFN or IFNAR component sequentially, via administration of an IFN/IFNAR covalent complex or via administration of an IFNAR/IFN fusion protein.

In a further embodiment, such enhanced bioavailability may also be accomplished by administering the IFNAR component alone, without adding any IFN. The IFNAR will form the "complex" in vivo with endogenous IFN and, thus, enhance the bioavailability, pharmacokinetics and/or pharmacodynamics of the endogenous IFN. This is particularly useful for the treatment of patients having a disease or condition which naturally causes the induction of native IFN, so that the IFN will already be circulating for its intended natural effect of fighting such disease or condition. The added IFNAR will potentiate the effects of the native IFN.

The preferred molecules for use in the complexes of the present invention have the sequence of a native IFN and IFNAR. The native sequence is that of a naturally occurring human IFN or IFNAR. Such sequences are known and can be readily found in the literature. Naturally occurring allelic variations are also considered to be native sequences.

The present invention also concerns analogs of the above IFNAR2/IFN complex of the invention, which analogs retain essentially the same biological activity of the complex having essentially the sequences of native IFNAR2 and IFN. Such analogs may be ones in which up to about 30 amino acid residues may be deleted, added or substituted by others in the IFNAR2 and/or IFN moieties of the complex, such that modifications of this kind do not substantially change the biological activity of the chimeric protein analog with respect to the complex itself. The various analogs may differ most from each other and from the basic complex molecule (that with essentially only naturally occurring IFNAR2 and IFN sequences) at the site of the linker peptide which joins the two moieties in the complex. As reported above, such a linker is preferably up to about 30 amino acids in length, and serves to separate the IFNAR2 and IFN moieties from each other in the complex. As regards such a linker, care should be taken to choose its sequence (and hence also to test biologically in appropriate standard assays each such analog) such that it will, for example, not result in incorrect folding of the complex, which may render it inactive or without enhanced activity, or render the complex analog immunogenic, which will elicit antibodies against it in a patient to be treated therewith with the result that such an analog will be ineffective at least as a medium- or long-term medicament. As regards the above analogs of the complex of the invention, these analogs are those in which one or more and up to about 30 of the amino acid residues of the basic complex of the invention are replaced by different amino acid residues, or are deleted, or one or more amino acid residues, up to about 30, are added to the original sequence of complex of the invention (that with essentially only the native IFNAR2/IFN sequences) without changing considerably the activity of the resulting products as compared with basic complex of the invention. These analogs are prepared by known synthesis and/or by site-directed mutagenesis techniques or any other known technique suitable therefor.

Any such analog preferably has a sequence of amino acids sufficiently duplicative of that of the basic IFNAR2/IFN complex such as to have substantially similar activity thereto. Thus, it can be determined whether any given analog has substantially the same activity and/or stability as the basic complex of the invention by means of routine experimentation, comprising subjecting each such analog to the biological activity and stability tests set forth in Examples 2–7 below.

Analogs of the complex which can be used in accordance with the present invention, or nucleic acid a sequence coding therefor, include a finite set of substantially corresponding sequences as substitution peptides or polynucleotides which can be routinely obtained by one of ordinary skill in the art, without undue experimentation, based on the teachings and guidance presented herein. For a detailed description of protein chemistry and structure, see Schulz. et al, *Principles of Protein Structure,* Springer-Verlag, New York (1978); and Creighton, T. E., *Proteins: Structure and Molecular Properties,* W. H. Freeman & Co, San Francisco (1983), which are hereby incorporated by reference. For a presentation of nucleotide sequence substitutions, such as codon preferences, see Ausubel et al (1987, 1992), §§A.1. I-A. 1.24, and Sambrook et al (1987, 1992), §§6.3 and 6.4, at Appendices C and D.

Preferred changes for analogs in accordance with the present invention are what are known as "conservative" substitutions. Conservative amino acid substitutions of those in the complex having essentially the naturally occurring IFNAR2 and IFN sequences, may include synonymous amino acids within a group which have sufficient similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues (Anfinsen, 1973). Analogs produced by such deletions and or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |

TABLE III-continued

Most Preferred Groups of Synonymous Amino Acids

| Amino Acid | Synonymous Group |
|---|---|
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Glu |
| Glu | Glu |
| Met | Met, Ile, Leu |
| Trp | Met |

Examples of production of amino acid substitutions in proteins which can be used for obtaining analogs of the complex IFNAR2/IFN for use in the present invention include any known method steps, such as presented in U.S. Pat. No. RE 33,653; U.S. Pat. Nos. 4,959,314; 4,588,585 and 4,737,462, to Mark et al; U.S Pat. No. 5,116,943 to Koths et al; U.S. Pat. No. 4,965,195 to Namen et al; and U.S. Pat. No. 5,017,691 to Lee, et al, and lysine substituted proteins presented in U.S. Pat. No. 4,904,584 (Shaw et al).

In another preferred embodiment of the present invention, any analog of the complex for use in the present invention has an amino acid sequence essentially corresponding to that of the above-noted basic complex of the invention. The term "essentially corresponding to" is intended to comprehend analogs with minor changes to the sequence of the basic complex which do not affect the basic characteristics thereof, particularly insofar as its ability to inhibit cancer cell proliferation or promote bone marrow transplantations, for example, is concerned. The type of changes which are generally considered to fall within the "essentially corresponding to" language are those which would result from conventional mutagenesis techniques of the DNA encoding the complex of the invention, resulting in a few minor modifications, and screening for the desired activity in the manner discussed above.

Preferably, the IFNAR2 portion of the complex will have a core sequence which is the same as that of the native sequence or biologically active fragment thereof, or a variant thereof which has an amino acid sequence having at least 70% identity to the native amino acid sequence and retains the biological activity thereof. More preferably, such a sequence has at least 85% identity, at least 90% identity, or most preferably at least 95% identity to the native sequence.

With respect to the IFN portion of the complex, the core sequence which may be used is the native sequence, or a biologically active fragment thereof, or a variant thereof which has an amino acid sequence having at least 70% identity thereto, more preferably, at least 85% or at least 90% identity, and most preferably at least 95% identity. Such analogs must retain the biological activity of the native IFN sequence or fragment thereof, or have antagonist activity as discussed hereinbelow.

The term "sequence identity" as used herein means that the sequences are compared as follows. The sequences are aligned using Version 9 of the Genetic Computing Group's GAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the claimed sequence.

Analogs in accordance with the present invention may also be determined in accordance with the following procedure. With respect to either the IFNAR portion of the complex or the IFN portion of the complex, the DNA of the native sequence is known to the prior art and is either found in the literature cited in the background section of the present specification or can be readily located by those of ordinary skill in the art. Polypeptides encoded by any nucleic acid, such as DNA or RNA, which hybridize to the complement of the native DNA or RNA under highly stringent or moderately stringent conditions, as long as that polypeptide maintains the biological activity of the native sequence or, in the case of IFN, either maintains the biological activity or possesses antagonistic activity, are also considered to be within the scope of the present invention.

Stringency conditions are a function of the temperature used in the hybridization experiment, the molarity of the monovalent cations and the percentage of formamide in the hybridization solution. To determine the degree of stringency involved with any given set of conditions, one first uses the equation of Meinkoth et al. (1984) for determining the stability of hybrids of 100% identity expressed as melting temperature Tm of the DNA-DNA hybrid: $Tm=81.5° C.+16.6(_{log}M)+0.41(\% GC)-0.61(\% form)-500/L$ where M is the molarity of monovalent cations, %GC is the percentage of G and C nucleotides in the DNA, % form is the percentage of formamide in the hybridization solution, and L is the length of the hybrid in base pairs. For each 1° C. that the Tm is reduced from that calculated for a 100% identity hybrid, the amount of mismatch permitted is increased by about 1%. Thus, if the Tm used for any given hybridization experiment at the specified salt and formamide concentrations is 10° C. below the Tm calculated for a 100% hybrid according to equation of Meinkoth, hybridization will occur even if there is up to about 10% mismatch.

As used herein, highly stringent conditions are those which are tolerant of up to about 15% sequence divergence, while moderately stringent conditions are those which are tolerant of up to about 20% sequence divergence. Without limitation, examples of highly stringent (12–15° C. below the calculated Tm of the hybrid) and moderately (15–20° C. below the calculated Tm of the hybrid) conditions use a wash solution of 2×SSC (standard saline citrate) and 0.5% SDS at the appropriate temperature below the calculated Tm of the hybrid. The ultimate stringency of the conditions is primarily due to the washing conditions, particularly if the hybridization conditions used are those which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6×SSPE), 5×Denhardt's reagent, 0.5% SDS, 100 μg/ml denatured, fragmented salmon sperm DNA at a temperature approximately 20° to 25° C. below the Tm. If mixed probes are used, it is preferable to use tetramethyl ammonium chloride (TMAC) instead of SSC (Ausubel, 1987, 1998).

"Functional derivatives" as used herein covers derivatives which may be prepared from the functional groups which occur as side chains on the residues or the N- or C- terminal groups, by means known in the art, and are included in the invention as long as they remain pharmaceutically acceptable, i.e., they do not destroy the biological activity of the corresponding protein of the complex as described herein and do not confer toxic properties on compositions containing it or the complex made therefrom. Derivatives may have chemical moieties, such as carbohydrate or phosphate residues, provided such a fraction has the same biological activity and remains pharmaceutically acceptable.

For example, derivatives may include aliphatic esters of the carboxyl of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (e.g., that of seryl or threonyl residues) formed with acyl moieties. Such derivatives may also include for example, polyethylene glycol side-chains which may mask antigenic sites and extend the residence of the complex or the portions thereof in body fluids.

The term "derivatives" is intended to include only those derivatives that do not change one amino acid to another of the twenty commonly-occurring natural amino acids.

The term "salts" herein refers to both salts of carboxyl groups and to acid addition salts of amino groups of the complex of the invention or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must have substantially similar biological activity to the complex of the invention or its analogs.

The term "biological activity" as used herein is interpreted s follows. Insofar as the IFNAR2 portion of the complex is concerned, the important biological activity is its ability to bind to Type I interferon. Thus, analogs or variants, salts and functional derivatives must be those chosen so as to maintain this interferon-binding ability. This can be tested by routine binding assay experiments. In addition, fragments of the IFNAR2, or analogs thereof, can also be used as long as they retain their interferon-binding activity. Fragments may readily be prepared by removing amino acids from either end of the interferon-binding polypeptide and testing the resultant for interferon-binding properties. Proteases for removing one amino acid at a time from either the N-terminal or the C-terminal of a polypeptide are known, and so determining fragments which retain interferon-binding ability involves only routine experimentation.

Additionally, the polypeptide which has such interferon-binding activity, be it IFNAR2, sINFAR2, an analog or variant, salt, functional derivative or fragment thereof, can also contain additional amino acid residues flanking the interferon-binding polypeptide. As long as the resultant molecule retains the interferon-binding ability of the core polypeptide, one can determine whether any such flanking residues affect the basic and novel characteristics of the core peptide, i.e., its interferon-binding characteristics, by routine experimentation. The term "consisting essentially of", when referring to a specified sequence, means that additional flanking residues can be present which do not affect the basic and novel characteristic of the specified sequence. This term does not comprehend substitutions, deletions or additions within the specified sequence.

While IFNAR2 or sIFNAR2 have been used throughout this description and in the examples, it should be understood that this is merely the preferred example and that the IFNAR1 subunit, and particularly its extracellular domain, may be substituted for IFNAR2 wherever IFNAR2 is referred to in the present disclosure. IFNAR1 can only be used in conjunction with interferons to which it binds. IFNAR1 is known to bind to IFNα. Any complex using IFNAR1 must be with a species of interferon, and preferably a species of IFNα, to which the IFNAR1 binds.

With respect to the interferon part of the complex of the present invention, the biological activity which must be maintained in any analog or variant, salt, functional derivative or fragment is the activity of the interferon relied upon for the intended utility. In most instances, this will be the ability to bind to a native cell surface receptor and thereby mediate signal production by the receptor. Thus, any such analog, derivative or fragment should maintain such receptor agonist activity to be useful in the present invention for such a utility. On the other hand, it is sometimes useful to have a molecule with antagonist activity on the receptor so as to prevent the biological activity of native interferon. Such an antagonist can also be used for prolonged beneficial effect by means of the complex of the present invention. For such utilities in which it is desired to eliminate an undesired effect of interferon, analogs which are still bound by the receptor and by the IFNAR portion of the complex but which do not mediate a signal and block signal generation by the native interferon on that receptor, may also be considered to be biologically active for the purpose of this invention and to be encompassed by the term interferon when used with respect to the complexes of the present invention. Straightforward assays can determine whether any such analog maintains such receptor agonist activity or has receptor antagonist activity and would, thus, be useful for one of the utilities of the present invention.

The present invention also concerns DNA sequences encoding the above complex of the invention and its analogs, as well as DNA vectors carrying such DNA sequences for expression in suitable prokaryotic or eukaryotic host cells. The ability to generate large quantities of heterologous proteins using a recombinant protein expression system has led to the development of various therapeutic agents, e.g., t-PA and EPO (Edington, 1995). The various expression hosts from which recombinant proteins can be generated range from prokaryotic in origin (e.g., bacteria) (Olins, 1993), through lower eukaryotes (e.g., yeast) (Ratner, 1989) to higher eukaryotic species (e.g., insect and mammalian cells (Reuveny, 1993; Reff, 1993). All of these systems rely upon the same principle—introducing the DNA sequence of the protein of interest into the chosen cell type (in a transient or stable fashion, as an integrated or episomal element) and using the host transcription, translation and transportation machinery to over-express the introduced DNA sequence as a heterologous protein (Keown, 1990).

In addition to the expression of native gene sequences, the ability to manipulate DNA at the nucleotide level has expedited the development of novel engineered sequences which, although based on natural proteins, possess novel activities as a result of the alteration in primary protein structure (Grazia, 1997).

Moreover, chosen sequences of DNA can be physically linked to generate transcripts which develop into novel fusion proteins where once independent proteins are now expressed as one polypeptide unit (Ibanez, 1991). The activity of such fusion proteins can be different, e.g., more potent, than either of the individual proteins (Curtis, 1991).

Human IFNβ is derived from a production process which uses the mammalian Chinese hamster ovary cell (CHO). Type 1 interferons can be expressed in a variety of host cells including bacteria (Utsumi, 1987), insect (Smith, 1983) and human (Christofinis, 1981). Human sIFNAR2 was also expressed using the CHO host cell. Alternatively, soluble receptors, such as sIFNAR2, have also been expressed successfully in bacterial expression systems (Terlizzese, 1996). The DNA for each gene was introduced into the CHO genome using a transfection procedure which resulted in recombination and integration of the expression vector. Cells which expressed the protein of interest were then isolated, cultured and the protein recovered and purified using standard industrial practices well known in the art.

The invention also concerns a pharmaceutical composition comprising as active ingredient an IFNAR2/IFN complex or analogs thereof or mixtures thereof or salts thereof and a pharmaceutical acceptable carrier, diluent or excipient. An embodiment of the pharmaceutical composition of the invention includes a pharmaceutical composition for enhanced IFN type action, in the treatment of viral diseases, in anti-cancer therapy, in immune modulation therapy and other applications of interferons and cytokines related thereto.

The pharmaceutical compositions of the invention are prepared for administration by mixing the complex or its analogs with physiologically acceptable carriers and/or stabilizers and/or excipients, and prepared in dosage form, e.g., by lyophilization in dosage vials. The method of administration can be via any of the accepted modes of administration for similar agents and will depend on the condition to be treated, e.g., intravenously, intramuscularly, subcutaneously, by local injection or topical application, or continuously by infusion, etc. The amount of active compound to be administered will depend on the route of administration, the disease to be treated and the condition of the patient. Local injection, for instance, will require a lower amount of the protein on a body weight basis than will intravenous infusion.

Free IFNβ has a tendency to oligomerize. To suppress this tendency, present day formulations of IFNβ have an acidic pH, which may cause some localized irritation when administered. As IFNAR can serve as a stabilizing factor for IFNβ and thereby prevent oligomerization, its use in IFNβ formulations can serve to stabilize the IFNβ and thereby obviate the necessity of acidic formulations. Accordingly, a non-acidic pharmaceutical composition containing IFNβ and IFNAR, along with other conventional pharmaceutically acceptable excipients, is also a part of the present invention.

The present invention also concerns uses of the complex of the invention or its analogs or mixtures thereof for anti-viral, anti-cancer and immune modulation therapy. Specifically, the interferon receptor-interferon complexes of this invention are useful for anti-viral therapy in such therapeutic indications as chronic granulomatous disease, condyloma acuminatum, juvenile laryngeal papillomatosis, hepatitis A and chronic infection with hepatitis B and C viruses.

In particular, the interferon receptor-interferon complexes of this invention are useful for anti-cancer therapy in such therapeutic indications as hairy cell leukemia, Kaposi's sarcoma, multiple myeloma, chronic myelogenous leukemia, non-Hodgkins's lymphoma and melanoma.

The interferon receptor-interferon complexes of this invention are also useful for immune modulation therapy, such as multiple sclerosis, rheumatoid arthritis, myasthenia gravis, diabetes, AIDS, lupus, etc.

Likewise, the present invention also concerns the complex or analogs thereof or mixtures thereof for use in the preparation of medicaments for treating the above-mentioned ailments or for use in the above noted indications.

The present invention will now be described in more detail in the following non-limiting Examples and the accompanying drawings.

EXAMPLES

Materials and Methods

ANTI-VIRAL WISH BIOASSAY and COMPLEX GENERATION

A WISH assay was developed based on the protocol of Novick et al (1982).

Materials

- WISH cells (ATCC CCL 25)
- Vesicular Stomatitis Virus stocks (ATCC V-520-001-522), stored at −70° C.
- IFNβ, human recombinant, InterPharm Laboratories LTD $90\times10^6$ IU/ml, specific activity: $264.5\times10^6$ IU/mg.
- Soluble human IFNAR2, 373 μg/ml stock concentration in PBS
- WISH Growth medium (MEM high glucose with Earls salts+10% FBS+1.0% L-glutamine+Penicillin/Streptomycin (100 U/ml, 100 μg/ml))
- WISH Assay medium (MEM high glucose with Earls salts+5% FBS+1.0% L-glutamine+Penicillin/Streptomycin (100 U/ml, 100 μg/ml), MTT at 5 mg/ml in PBS, stored at −70° C.

Methods

- Dilute recombinant human IFNβ to 19 IU/ml (4× the predetermined $EC_{50}$ dose) in WISH assay medium.
- Starting at 90 μg/ml, make eleven (11) three-fold dilutions of human recombinant sIFNAR2 in Eppindorf tubes in WISH assay medium. Twelfth tube contains WISH assay medium only.
- Add 25 μl of IFNβ to each well in a flat-bottomed 96-well plate (add 25 μl of WISH assay medium alone to one 3×12 well section to control for IFNAR2 effects in the absence of IFNβ).
- Add 25 μl of each dilution of the sIFNAR2 (or assay medium only in row twelve) in triplicate down the twelve rows of the 96-well plate.
- Preincubate IFNβ with sIFNAR2 for 1–4 hours in 37° C. incubator prior to the addition of WISH cells.
- Harvest log growth phase WISH cells with trypsin/EDTA solution, wash in WISH assay medium, and bring to a final concentration of $0.8\times10^6$ cells/ml.
- Add 50 μl of WISH cell suspension ($4\times10^4$ cells per well) to each well. Final concentration of both IFNβ and IFNAR2 is that which is exposed to the cells, so that the final concentration of IFNβ is 4.75 IU/ml (1×), and the final concentration of sIFNAR2 in row one is 22.5 μg/ml.
- After incubation for 24 hours in a 5% $CO_2$ humidified incubator, 50 Al of a 1:10 dilution (in WISH assay medium) of VSV stock (a dose predetermined to lyse 100% of WISH cells within 48 hours) is added to all wells except for the no virus control wells (these receive an equal volume of assay medium only).

After an additional 48 hours, 25 μl of MTT solution is added to all wells, after which plates are incubated for an additional 2 hours in the incubator.

Contents of wells are removed by plate inversion, and 200 μl of 100% ethanol is added to wells.

After 1 hour, plates are read at 595 nm using the Soft max Pro software package and Spectramax spectrophotometer system (Molecular Devices).

All sequencing reactions were performed using the ThermoSequenase™ radiolabeled terminator cycle sequencing kit (Amersham Life Science; Cleveland, Ohio). The protocols supplied by the manufacturer were used. All sequencing reactions were analyzed on CastAway™ Precast sequencing gels (Stratagene; LaJolla, Calif.) that contained 6% polyacrylamide and 7M urea. Sequencing reactions were loaded in the order A-C-G-T. Autoradiographs of the sequencing gels were read manually. The Genetics Computer Group Sequence Analysis Software Package and UNIX workstation were used for DNA sequence analysis.

Example 1

To assess the anti-viral activity of the human IFNAR2/IFNβ complex and human IFNAR2Ig-IFNβ complex, a fixed concentration of IFNβ (4.75 IU/ml) was preincubated for 3 hours at 37° C. with human sIFNAR2 (recombinant p40) or human IFNAR2Ig at varying concentrations (0.25–30000 ng/ml) and then tested in a WISH-VSV cytopathicity assay. In the absence of IFN no anti-viral protection was detected (data not shown).

Anti-viral activity of Type I interferons (used at predetermined $EC_{50}$ concentrations) in the presence of approximately 30 ng/ml sIFNAR2 reveals optimal agonist activity with IFNβ, but not alone. Anti-viral activity was measured by MTT conversion 48 h after VSV challenge.

When IFN was present at an expected $ED_{50}$ concentration, protection was observed (see FIG. 1; absorbance equal to 0.45, no protection absorbance equals ~0.0, complete protection absorbance equals ~1.8)). When IFNAR2 or IFNAR2Ig was titrated in at varying concentrations there was ~4× enhancement in the activity of IFNβ up to 32 ng/ml of IFNAR2 and IFNAR2Ig (see also Example 2 and FIG. 2). Above 32 ng/ml IFNAR or IFNAR2Ig, IFNβ activity decreased as expected, presumably due to competition for IFNβ of the sIFNAR with the membrane based IFNAR. This experiment, thus, provides support for the increased potency and enhanced activity of IFNβ in the IFNAR2-IFN complex.

Example 2

Figure 2:
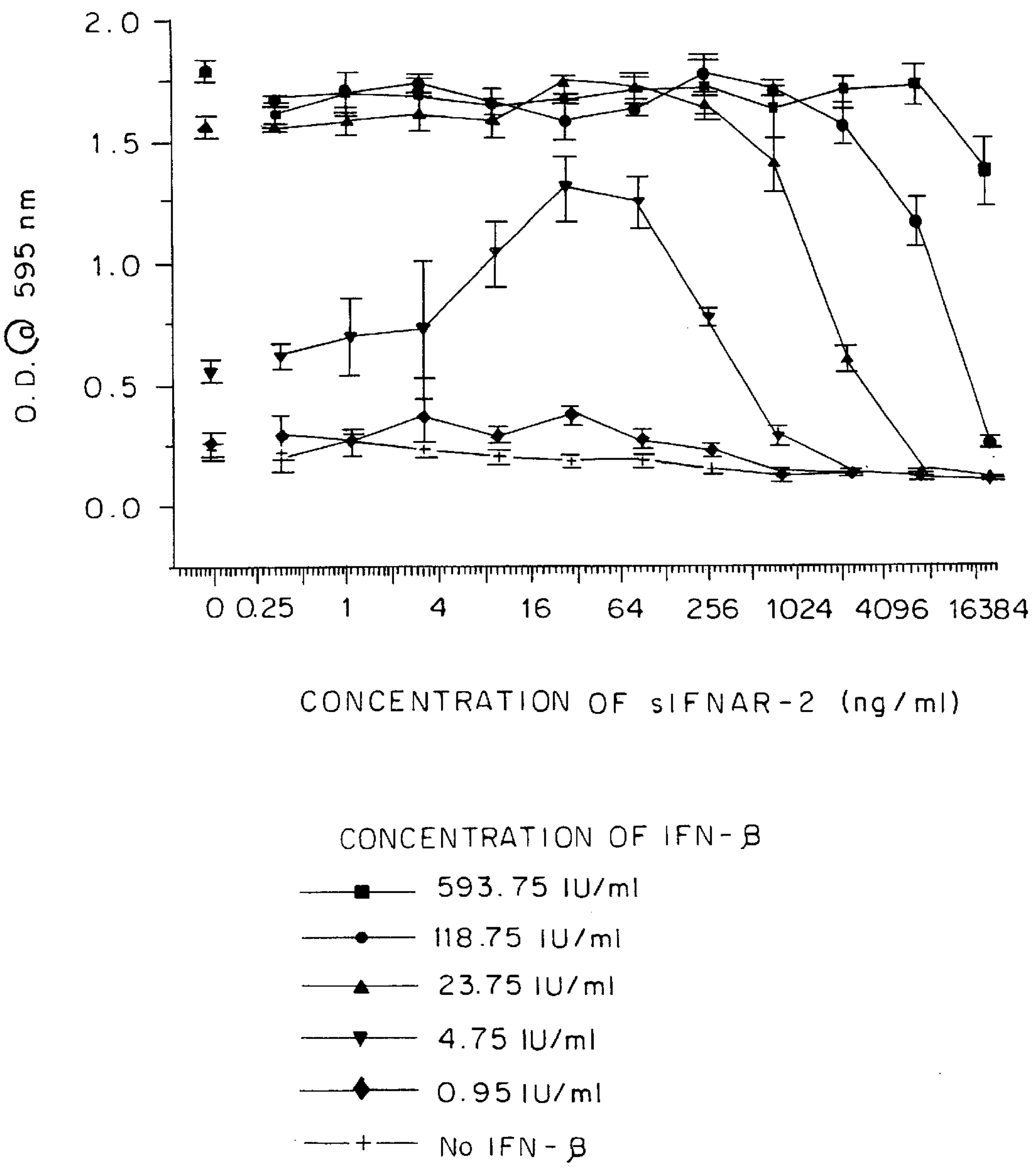
FIG. 2 is a graph showing anti-viral activity of sIFNAR2 and IFNβ at a sub-optimal dose of IFNβ. Synergistic anti-viral activity of IFNβ and sIFNAR2 following one hour preincubation is revealed at an intermediate IFNβ dose.

The effect of changing the IFNβ concentration on sIFNAR2/IFN complex activity was examined at different concentrations of IFNβ in addition to the $ED_{50}$. As can be seen in FIG. 2, at 4.75 IU/ml IFNβ, IFNAR2 preincubation for 1 hour enhanced the activity of IFNβ by ~2× at a concentration maximum of ~32 ng/ml. At each of the higher concentrations of IFNβ it was not possible to detect enhancement of the IFNβ anti-viral activity as the activity was already maximal. These results also support that an IFNAR2/IFNβ complex has enhanced IFN activity.

Example 3

Figure 3:
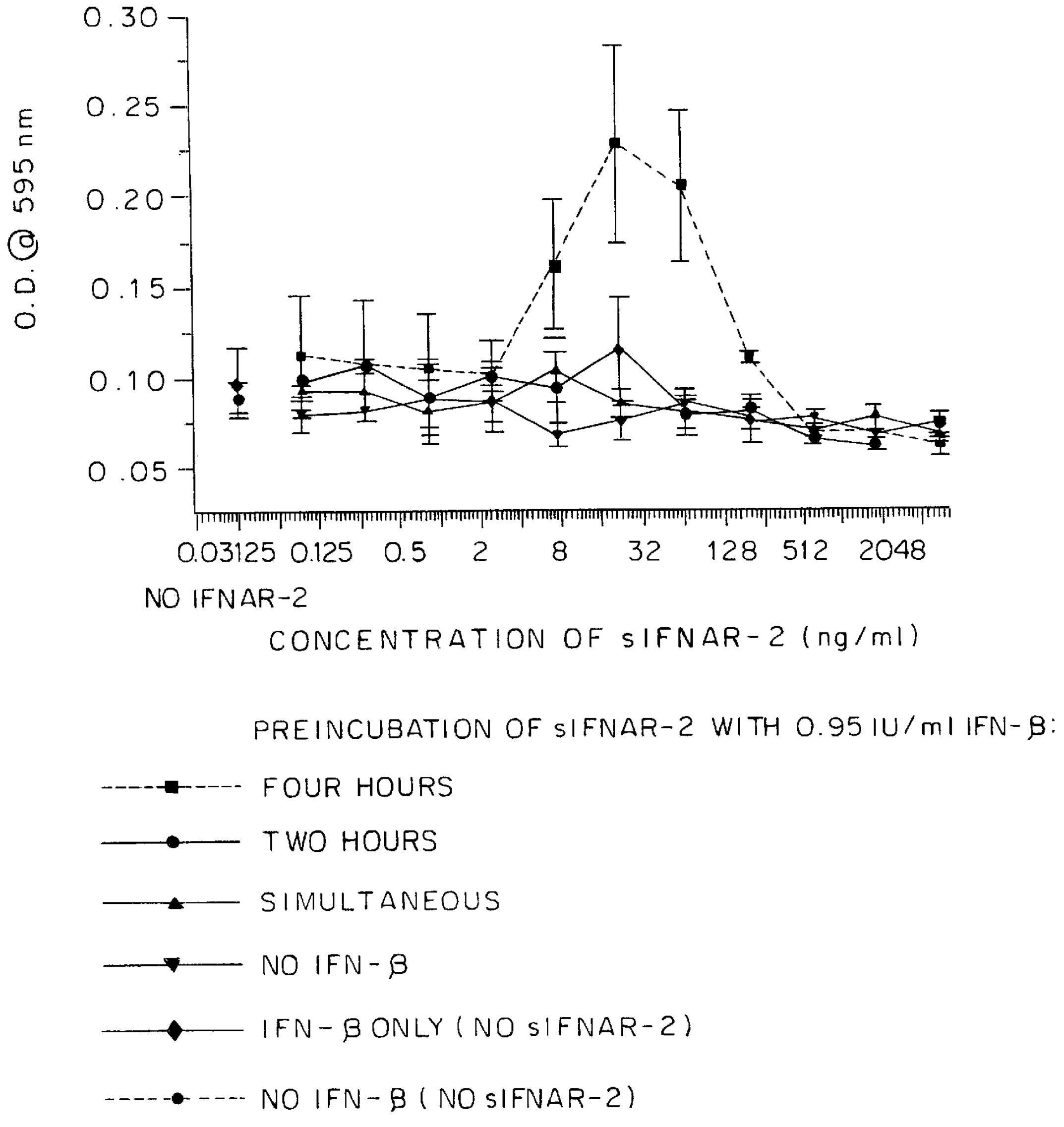
FIG. 3 is a graph showing anti-viral activity of sIFNAR2 and a sub-effective dose of IFNβ (0.95 IU/ml) as a function of preincubation time. WISH cells were exposed to IFNβ (0.95 IU/ml sub-effective dose) and sIFNAR2, following a preincubation at the indicated times. Synergistic anti-viral activity is observed only after 4 hours of preincubation. Anti-viral activity was measured by MTT conversion 48 hours after VSV challenge. At sub-therapeutic levels of IFNβ, formation of the IFNAR2/IFN complex results in enhanced anti-viral activity.

The kinetics of the IFNAR2/IFNβ complex formation was examined by assessing the anti-viral activity of a sub-effective concentration of IFNβ (0.95 IU/ml) at various times of preincubation with different concentrations of IFNAR2. As seen in FIG. 3, 4 hours of preincubation were necessary to give enhanced anti-viral activity of IFNβ at this sub-effective dose. Thus, at levels of IFNβ which are inactive by themselves, addition of IFNAR2 to generate a complex resulted in significant IFN anti-viral activity. This experiment provides additional support for the IFNAR2/IFNβ complex enhanced IFN activity.

Example 4

It has been established that IFNβ bioactivity rapidly declines following in vitro reconstitution at 37° C. (physiologic saline buffer pH 7.4). This is, at least in part, due to the formation of IFNβ oligomeric structures which have reduced activity. To test whether IFNAR2 enhances the stability of IFNβ at physiologic pH, an experiment was conducted in which varying concentrations of IFNβ were incubated alone (in RPMI 1640 media, Gibco) or in the same media in the presence of IFNAR2 at a constant ratio of IFNAR2 to IFNβ (2.5 ng/IU).

IFNβ (500 IU/ml) was preincubated with an equal volume of either sIFNAR2 (1.25 μg/ml) or RPMI only, for 3 hours at 37° C. Titration of both IFNβ solutions was performed in WISH assay medium in a 96-well plate prior to the addition of WISH cells. VSV was added after 24 hours and was assessed after an additional 48-hour incubation as determined by MTT conversion.

Figure 4:
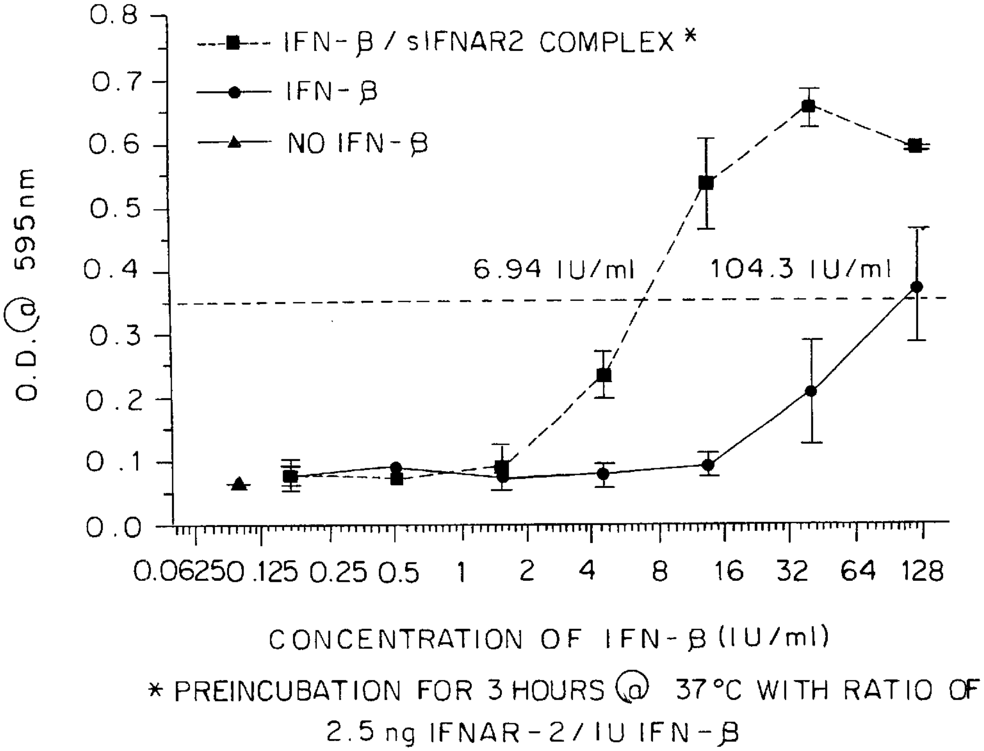
FIG. 4 is a graph showing enhanced anti-viral activity of human IFNβ following preincubation with sIFNAR2.

As seen in FIG. 4, IFNβ alone has an $ED_{50}$ of ~104 IU/ml, while preincubation of IFNR with soluble IFNAR2 results in a significantly enhanced $ED_{50}$=~7 IU/ml. The high $ED_{50}$ of IFNβ alone may be due to the oligomerization of IFNβ in solution. The above results again show the enhanced stability of IFNβ when complexed with IFNAR2.

Example 5

To assess whether enhanced activity of IFNβ in the presence of IFNAR2 is due to specific protection by sIFNAR, the activity of IFNβwas evaluated following complexation with IFNAR2 or other unrelated proteins at the same concentration (human IgG, bovine serum albumin (BSA)).

Figure 5:
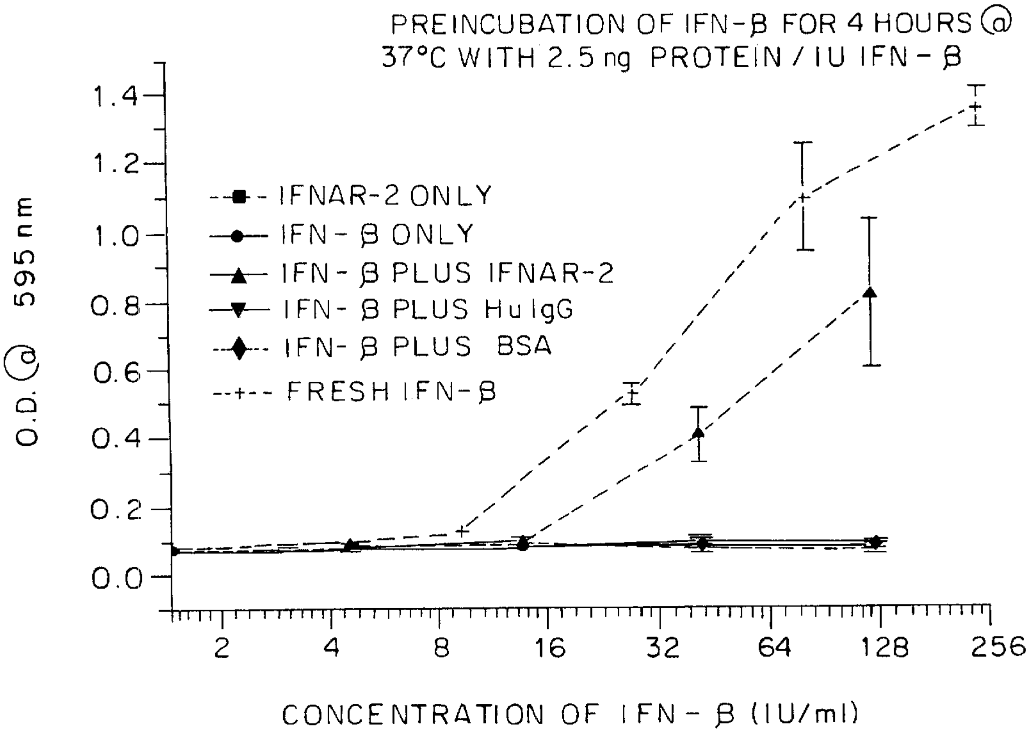
FIG. 5 is a graph showing that enhanced anti-viral activity of human IFNβ associated with sIFNAR is specific for IFNAR2 but not other proteins.

As shown in FIG. 5, IFNβ (500 IU/ml) was preincubated with an equal volume of either the indicated proteins (1.25 μg/ml) or RPMI only, for 4 hours at 37° C. Titration of these IFNβ solutions in WISH assay medium was performed in a 96-well plate prior to the addition of WISH cells. Freshly-prepared IFNβ was also included to determine the effect of the preincubation on IFNβ activity. VSV was added after 24 hours, and CPE was assessed after an additional 48 hour incubation as determined by MTT conversion.

Preincubation of IFNβ with non-specific proteins (i.e., BSA or human IgG) at 2.5 ng/IU IFNβ did not protect the activity of IFNβ after reconstitution. The activity of the IFNAR2/IFNβ complex in this assay was similar to freshly added IFNβ, which supports the finding that sIFNAR2 stabilizes IFNβ activity.

Example 6

Figure 6:
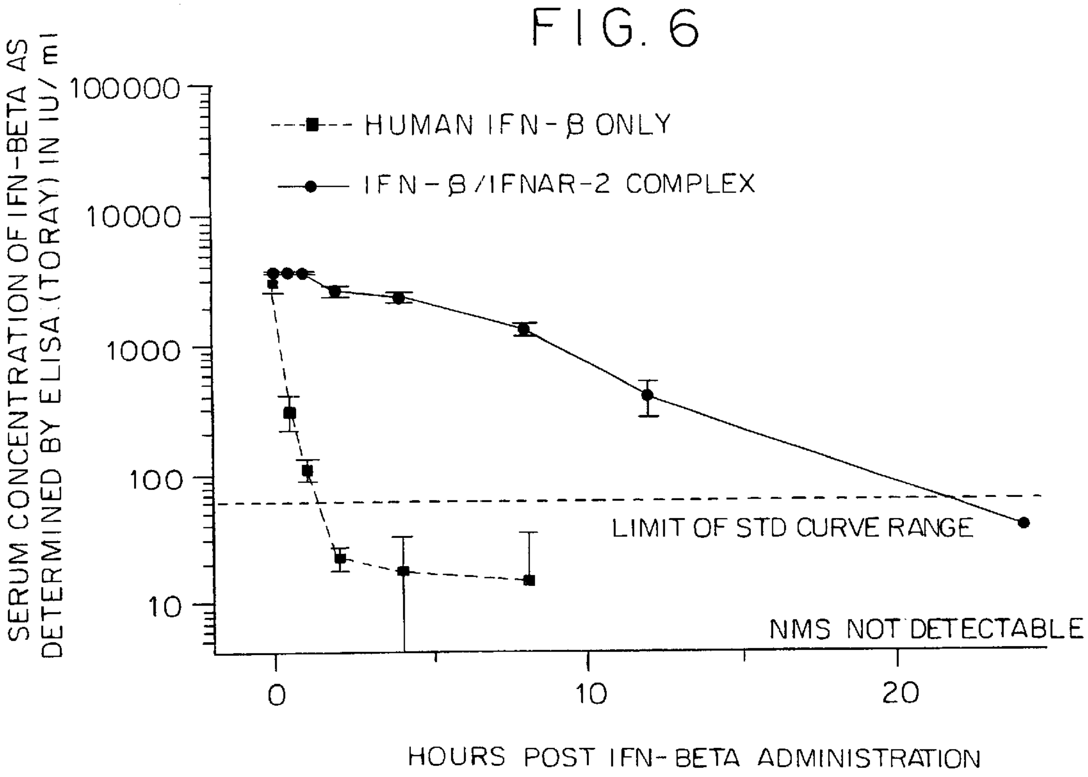
FIG. 6 is a graph showing the pharmacokinetic comparison of human IFNβ and IFNβ/IFNAR2 complex in mice as determined by ELISA.
Figure 7:
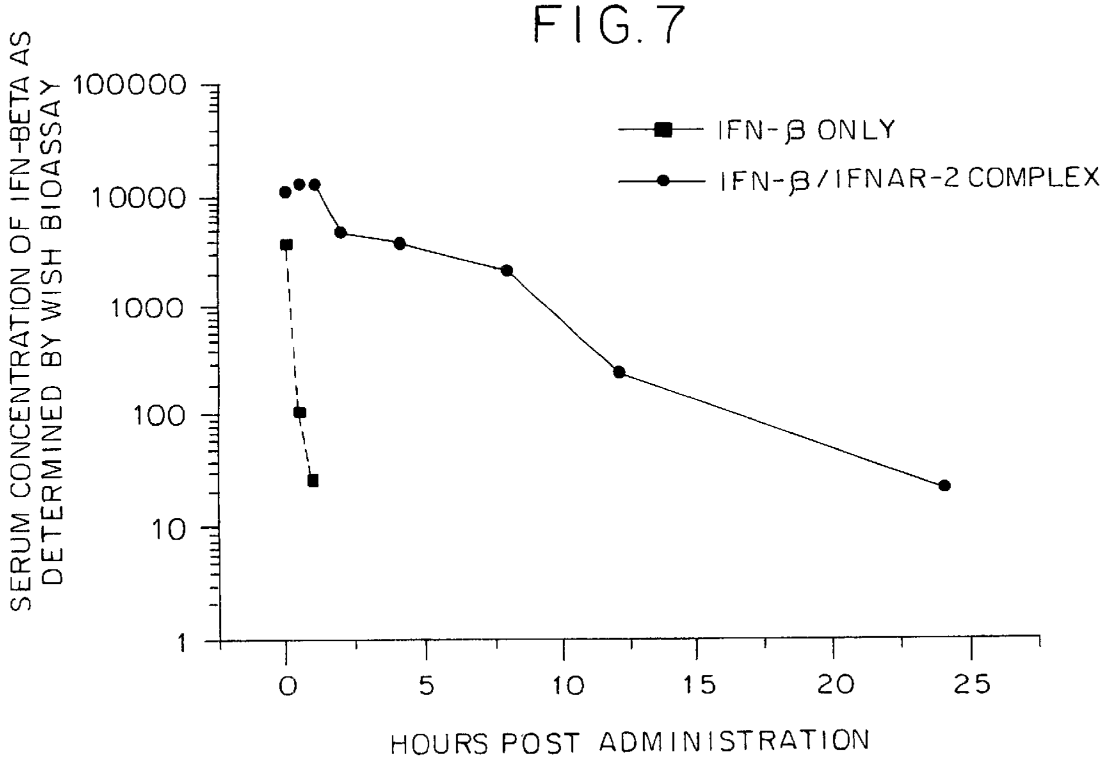
FIG. 7 is a graph showing the pharmacokinetic comparison of human IFNβand IFNβ/IFNAR2 complex in mice as determined by bioassay.

IFNAR2/IFNβ complex showed a greatly prolonged pharmacokinetic profile of IFNβ in the mouse based on ELISA and bioassay analysis (FIGS. 6 and 7).

B6D2F1 strain mice received a single intravenous bolus injection of either human IFNβ ($2.5\times10^6$ IU/kg) or the same concentration of IFNβ preincubated for 1 hour at 4° C. with human IFNAR2 (2.5 ng/IU of IFN). Sera were collected 0.05 to 48 hours post-administration from the retro-orbital plexus, and IFNβ concentration and IFNβ anti-viral activity was assessed by ELISA (FIG. 6) or WISH bioassay (FIG. 7), respectively. Serum concentrations falling below the level of assay sensitivity (7.55 IU/ml) in the ELISA assay were not plotted.

Not only did the complex show an extended pharmacokinetic profile, but by WISH anti-viral assay the level of biologically active IFNβ in the mouse was greatly enhanced over time, thus showing the enhanced stability and elongated plasma half-life of the IFNAR2/IFNβ complex of the invention with respect to IFNβ alone.

Example 7

Figure 8:
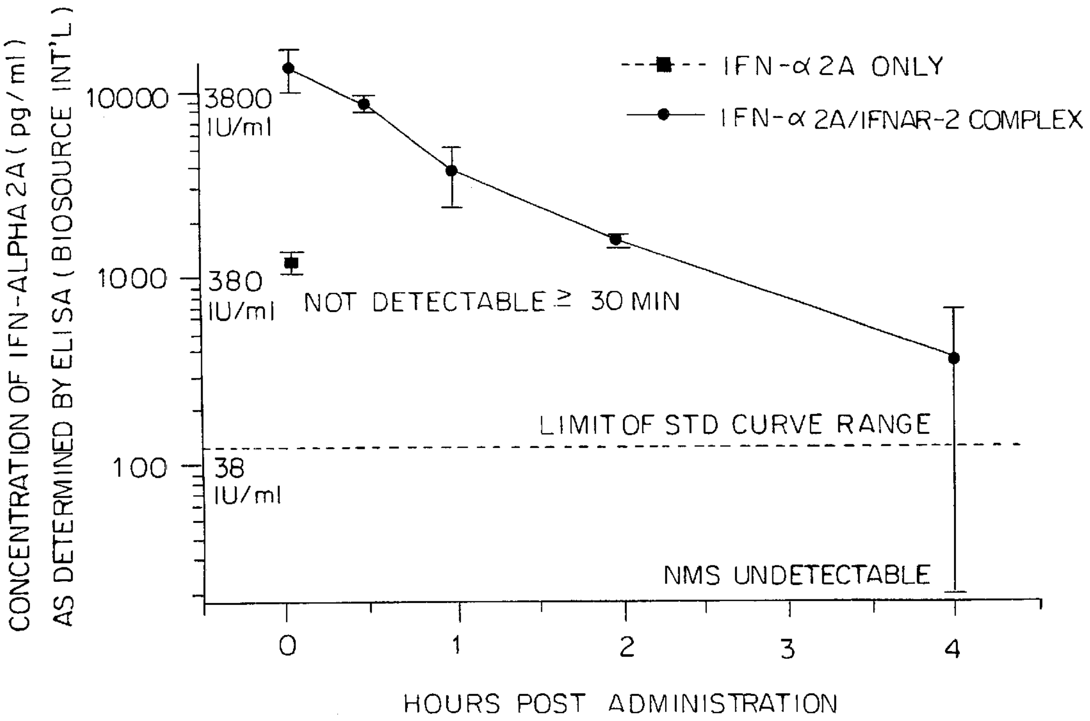
FIG. 8 is a graph showing the pharmacokinetic comparison of human IFNα and IFNα/IFNAR2 complex in mice as determined by ELISA.
Figure 9:
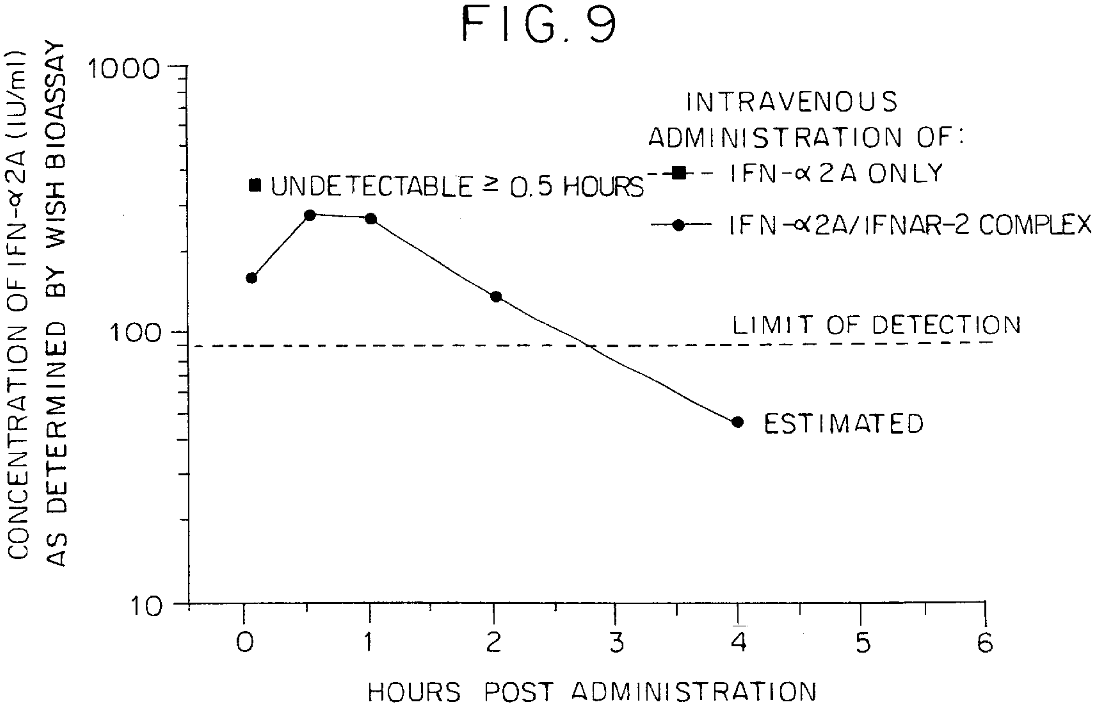
FIG. 9 is a graph showing the pharmacokinetic comparison of human IFNα and IFNα/IFNAR2 complex in mice as determined by bioassay.

IFNAR2/IFNα2a complex showed a greatly prolonged pharmacokinetic profile of IFNα2a in the mouse based on ELISA and bioassay tests (FIGS. 8 and 9).

B6D2F1 strain mice received a single intravenous bolus injection of either human IFNα ($1.25 \times 10^5$ IU/kg) or the same concentration of IFNα preincubated for 1 hour at 4° C. with human IFNAR2 (14.9 ng/IU of IFN). Sera were collected at indicated times from the retro-orbital plexus, and IFNα2a concentration and IFNα anti-viral activity was assessed by ELISA (FIG. 8) or WISH bioassay (FIG. 9), respectively.

IFNα was assessed by ELISA specific for human IFNα. Serum concentrations falling below the level of assay sensitivity (30 IU/ml) in the ELISA were not plotted.

Not only did the complex show an extended pharmacokinetic profile for IFNα, but by WISH anti-viral assay the level of biologically active IFNα in the mouse was greatly enhanced over time, thus showing the enhanced stability and elongated plasma half-life of the IFNAR2/IFN complex of the invention with respect to IFNα alone.

Example 8

Engineering of IFNAR2/IFN Fusion Proteins. Constructs were engineered so that the C-terminal of the IFNAR2 extracellular domain is fused to the N-terminus of the mature IFN using the following peptide linkers, with G and S representing the amino acids glycine and serine, respectively:

IFNAR2extracellular (linker) mature IFNβ

. . . ESEFS$(GGGGS)_n$MSY . . . , where n=0 (SEQ ID NO:15), 1 (SEQ ID NO:7), 2 (SEQ ID NO:6), 3 (SEQ ID NO:5), 4 (SEQ ID NO:4), and 5 (SEQ ID NO:3)

The full amino acid sequence of the n=2 IFNAR2/IFNβ fusion is shown in FIG. 10 (SEQ ID NO:14).

The expression vector pSVEIF, which contained the gene expressing human recombinant IFN, was used as the template for PCR. Synthetic primers were designed so that only the mature protein coding region of human IFN (MSY . . . ) could be amplified from the template. The 5' primer consisted of sequences for a digested-SmaI site, the last seven amino acids of IFNAR2 (GQESEFS) (residues 344–349 of SEQ ID NO:14), and the $(GGGGS)_1$ (SEQ ID NO:1) linker. BamHI and XhoI sites were also introduced in the 5' PCR primer to facilitate cloning of the other cassettes. The 3' primer contained an AvrII site immediately following the TGA stop codon of hIFNβ. The PCR contained approximately 1 g of template DNA, 1 g of each PCR primer, 0.2 mM each of dATP, dCTP, dGTP, and dTTP, 1×ThermoPol Reaction Buffer (10 mM KCl, 20 mM Tris-HCl, (pH 8.8 at 25° C.), 10 mM $(NH_4)_2SO_4$, 2 mM $MgSO_4$, 0.1% Triton X-100: New England Biolabs; Beverly, Mass.), and 3 mM $MgSO_4$ (5 mM $MgSO_4$ final concentration) in a reaction volume of 100 $\mu$l. After an VENTR® initial incubation at 99.9° C. for 30 seconds, 2 units of VENTR® DNA polymerase was added to the reaction. PCR consisted of 20 cycles of the following: (a) 99.9° C. for 30 seconds, (b) 65° C.–55° C. for 30 seconds, decreasing 0.5° C. with each cycle, and (c) 75° C. for 40 seconds. An additional 15 cycles were done with the above profile but with the annealing temperature held at 55° C. The PCR reactions were purified using the Wizard™ PCR Preps DNA Purification System (Promega; Madison, Wis.). After digestion of the PCR products with AvrII, the reactions were purified on low melting point agarose gels. The gel-purified fragment containing the hIFNβ mature protein sequence with 1 GS linker was ligated into the (SmaI+AvrII)-digested expression vector pCMV-p40, which contained the gene coding for the soluble form of human recombinant IFNAR2. The ligation reactions were used to transform competent *E. coli* XL-1 Blue cells using standard methods (Sambrook et al, 1989). Correct assembly of the construction, called pCMV-IFNAR2-IFNα GS, was confirmed by restriction endonuclease digestion and sequencing of the PCR-generated region of the "Interfusion". Subsequent constructs were engineered by using oligonucleotide cassettes, each containing a BamHI overhang, the appropriate $(GGGGS)_n$ linker (SEQ ID NO: 1 when n=1) and a XhoI overhang. The 0 GS cassettes contained SmaI and XhoI overhangs. After confirmation of the pCMV-IFNAR2/IFNAβ 1 GS vector, it was digested with BamHI and XhoI, and the appropriate cassettes were ligated into this vector. For the 0 GS construct, the vector was digested with SmaI and XhoI for ligation of the cassette.

Figure 11:
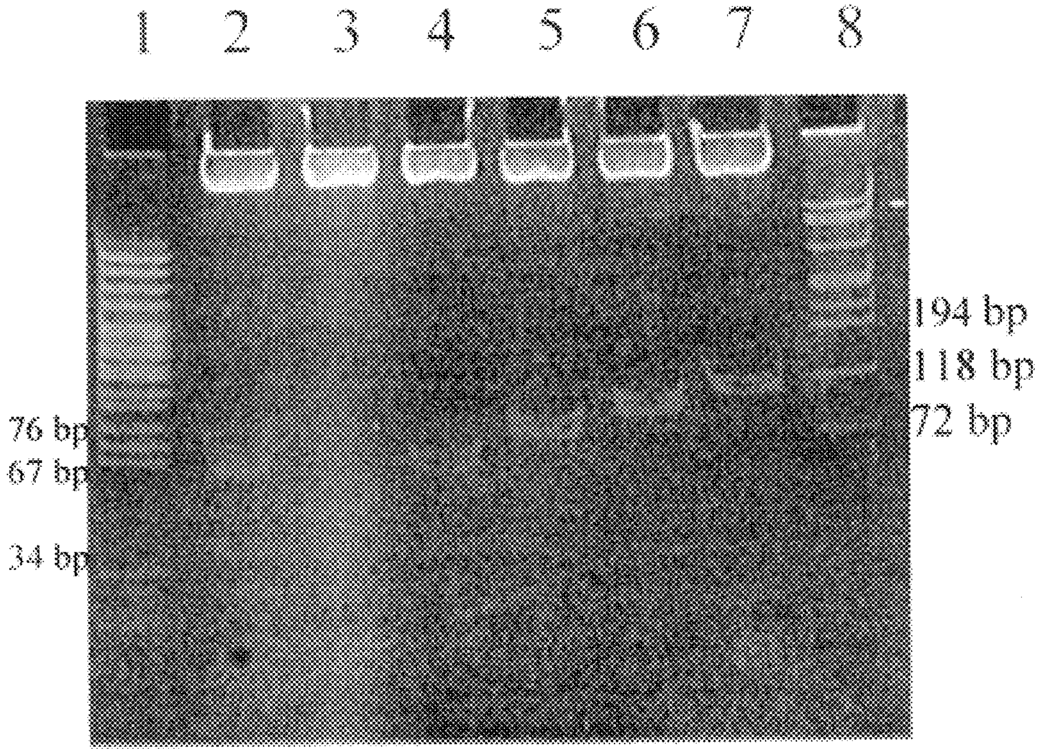
FIG. 11 is a gel showing the restriction enzyme analysis of pCMV-IFNAR2/IFNβ; 10% PAG, Lanes 3–7: BamHI/XhoI digests; Lane 2: SmaI/XhoI digest; Lane 1: pBR322 DNA-MspI digest marker; Lane 2: pCMV-IFNAR2-IFNβ, 0GS; Lane 3: 1GS; Lane 4: 2GS; Lane 5: 3GS; Lane 6: 4GS; Lane 7: 5GS; Lane 8: ϕX174 RFDNA HaeIII digest marker.

A total of six vectors were created, pCMV-IFNAR2/IFNβ n (GS), where n represents 0, 1, 2 ,3, 4, or 5 GGGGS (SEQ ID NO:1) linker units. These restriction digestion results are shown in FIG. 11. Sequencing primers were designed so that the cassette for each construct was sequenced in full. Large scale plasmid DNA cultures were prepared for each of the confirmed constructs using a commercially available kit and the protocols described by the manufacturer (Qiagen; Chatsworth, Calif.).

Figure 12:
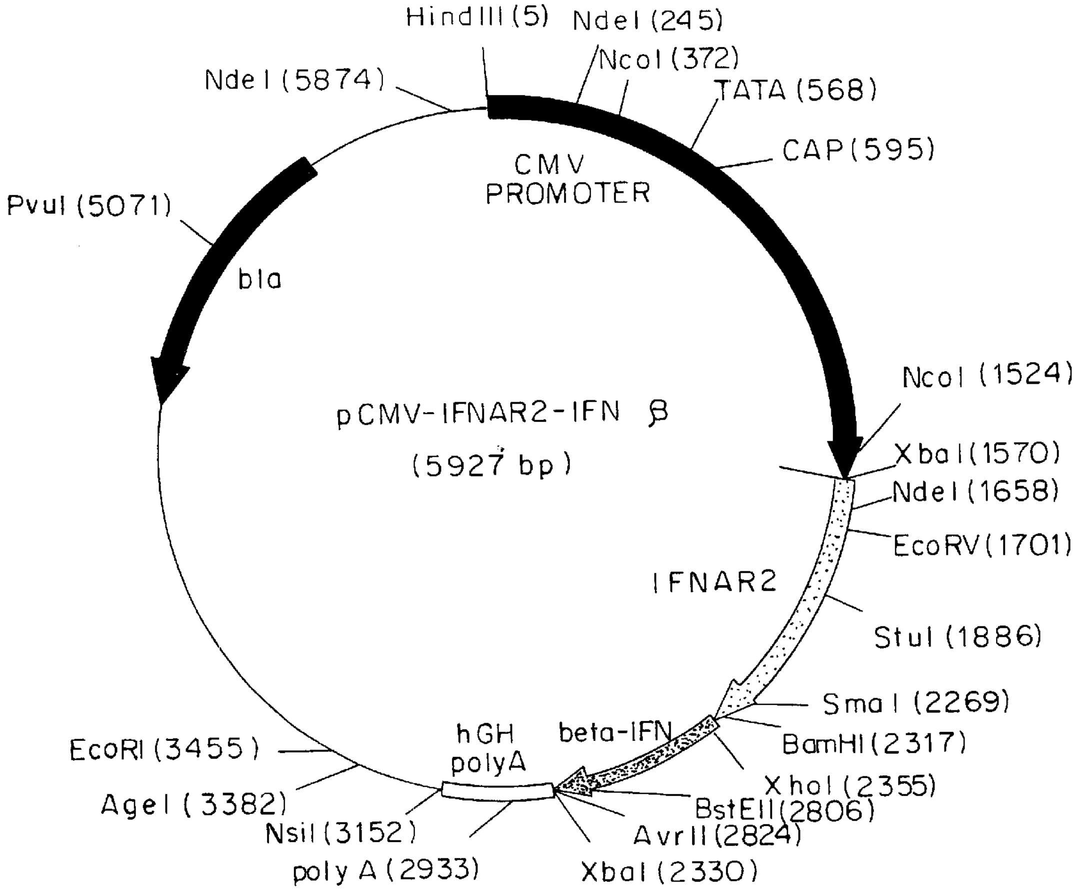
FIG. 12 is the restriction endonuclease map of the IFNAR2/IFNβ expression vector.

FIG. 12 is a representative plasmid map of the pCMV-IFNAR2/IFNAβ "Interfusion" expression vectors. Transcription of the IFNAR2/IFNβ fusion protein is directed by the human immediate early CMV promoter. The human growth hormone (hGH) polyadenylation signal sequence provided by the vector was used for 3' processing of the IFNAR2/IFNβ transcripts.

List of Vectors

| No. | Name | Exp. Vector | GGGGS (SEQ ID NO: 1) Linker |
|---|---|---|---|
| 1 | pCMV-IFNAR2-IFNβ, 0GS | pCMV.PA4 | N/A |
| 2 | pCMV-IFNAR2-IFNβ, 1GS | pCMV.PA4 | One |
| 3 | pCMV-IFNAR2-IFNβ, 2GS | pCMV.PA4 | Two |
| 4 | pCMV-IFNAR2-IFNβ, 3GS | pCMV.PA4 | Three |
| 5 | pCMV-IFNAR2-IFNβ, 4GS | pCMV.PA5 | Four |
| 6 | pCMV-IFNAR2-IFNβ, 5GS | pCMV.PA4 | Five |

Sequence data was obtained for the PCR-generated region of IFNAR2/IFNβ 1GS fusion; this data showed that the sequence was as predicted. Sequence data was obtained for the peptide linker region of the other constructions; the sequences were also as predicted.

A Northern blot analysis was performed on cells transfected with each construct. A band of approximately 1.4 kb in size was present in all lanes containing the IFNAR2/IFNβ n GS samples for both the IFNAR2 probe and for the IFNβ probe. With the IFNβ probe, an additional band of approximately 0.9 kb is observed. A band of this size would correspond to an alternatively spliced transcript that would contain the last six amino acids of IFNAR2, the (n) GS peptide linker, and the hIFN mature protein coding sequence. This was confirmed by sequencing cDNA prepared from the total RNA isolated from the transiently transfected CHO cells of Example 9.

Example 9

Transient Transfection. CHO-DUKX cells are a clonal mutant of Chinese hamster ovary cells lacking dihydrofolate reductase activity (Urlaub et al (1980); Graff et al (1982)). The cells were maintained in Alpha Minimum Essential Medium (αMEM) plus ribonucleosides and dexoyribonucleosides, supplemented with 10fetal bovine serum (FBS) and 1% L-glutamine (complete medium). A transient transfection was done using the Lipofectamine PLUS™ Reagent (GibcoBRL Life Technologies; Gaithersburg, Md.) and the protocol provided by the manufacturer. Approximately 24 hours prior to transfection, cells were plated in 100 mm diameter dishes at a density of $2\times10^6$ cells/dish. For the transfection, 4 μg of the supercoiled vector plasmid DNA (pCMV-IFNAR2-IFN n GS, where n=0, 1, 2, 3, 4, or 5) was used. The serum-free medium provided by the manufacturer was used for dilution of the DNA and PLUS reagent. Cell supernatants were collected after incubation at 37° C. for 48 hours in complete medium for ELISAs (IFNAR2, IFNβ) and Western gels.

RNA Extraction and Northern Analysis. Total cellular RNA (Chomczynski et al, 1987) was extracted from the transiently transfected CHO-DUKX cells. Ten g of total RNA per lane was size-fractionated in agarose gels which contained formaldehyde as a denaturant. Samples were loaded in duplicate sets. The RNA was transferred to GeneScreen Plus nylon membranes (DuPont/NEN Medical Products; Boston, Mass.) by capillary blot in 10×SSC (1.5M sodium chloride, 0.15M sodium citrate). The immobilized RNA was hybridized to $^{32}$P-labeled hIFNAR2 and hIFNβ PCR fragments in a solution modified from that of Church and Gilbert (1984). The buffer contained 0.25M sodium phosphate, pH 7.2, 0.25M sodium chloride, 7% sodium dodecyl sulfate (SDS), 1 mM ethlylenediaminetetraacetic acid and 100 μg/ml *E. coli* tRNA. The $^{32}$P-labeled probes were generated using a commercially available kit ("High Prime" Boehringer Mannheim; Indianapolis, Ind.) and the procedures described therein. Non-incorporated radioactivity was removed by chromatography on Sephadex G-50 columns. After hybridization, the blots were washed; the most stringent condition used was 0.2×SSC, 0.1% SDS at 65° C. The blots were subjected to autoradiography.

Expression of the Interfusion Proteins. Supernatants from each of the Interfusion constructs transiently transfected into CHO cells were analyzed for IFNAR2 and IFNβ expression levels using an IFNAR2 specific ELISA and an IFNβ ELISA (Toray), respectively. The results of this analysis are shown below in Table IV.

TABLE IV

Interfusion Constructs Transiently Transfected into CHO Cells

| Sample Identification | [hIFNβ]*, (U/ml) | [hIFNAR2]†, (ng/ml) | [hIFNβ]‡, (μg/ml) | [hIFNβ]#, (pmols) | [hIFNAR2]§, (pmols) | IFN/IFNAR |
|---|---|---|---|---|---|---|
| 0GS | 29,175 | 1094 | 0.146 | 6.571 | 31.802 | 0.207 |
| 1GS | 24,906 | 994 | 0.125 | 5.609 | 28.895 | 0.194 |
| 2GS | 13,597 | 600 | 0.068 | 3.063 | 17.442 | 0.175 |
| 3GS | 14,998 | 718 | 0.075 | 3.378 | 20.857 | 0.162 |
| 4GS | 9,998 | 535 | 0.050 | 2.251 | 15.538 | 0.145 |
| 5GS | 9,597 | 540 | 0.048 | 2.161 | 15.698 | 0.138 |
| IFNAR2 | Not Found | 1176 | | | 34.200 | |
| Culture Medium | Not Found | 0 | | | | |

*Determined using the TORAY kit
†Determined using the hIFNAR2 ELISA
‡Based on a specific activity of $2.0 \times 10^5$ U/mg ($2 \times 10^8$/mg)
#Based on a mass of 22,200 daltons (average mass by MALDITOF analysis of hIFNβ)
§Based on a mass of 34,400 daltons (average mass by MALDITOF analysis)

As can be seen, with increasing linker length a decrease in detectable IFNAR2 and IFNβ was observed. At this time it is not possible to establish whether this is due to a decrease in the amount of Interfusion protein expressed as the linker length increases or whether, as the linker length increases, the IFNβ can bind in the IFNAR2 binding site and, therefore, is not completely detectable by the ELISA assays. It is known that the IFNβ assay only detects non-complexed IFNβ.

Figure 13:
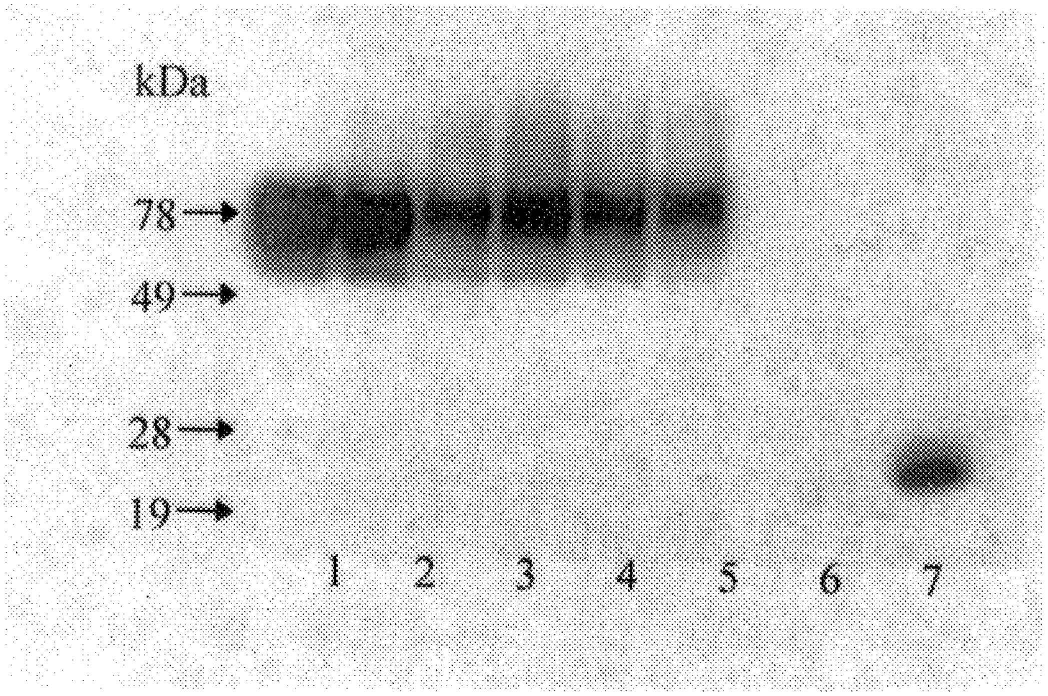
FIG. 13 is the Western blot analysis of IFNAR2/IFNβ fusion protein. Lane 1, IFNAR2/IFNβ construct containing no linker; lane 2, IFNAR2/IFNβ construct containing one $Gly_4Ser$ (SEQ ID NO:1) linker; lane 3, IFNAR2/IFNβ construct containing two $Gly_4Ser$ (SEQ ID NO:1) linkers; lane 4, IFNAR/IFNβ construct containing three $Gly_4Ser$ (SEQ ID NO:1) linkers; lane 5, IFNAR/IFNβ construct containing four $Gly_4Ser$ (SEQ ID NO:1) linkers; lane 6, IFNAR/IFNβ construct containing five $Gly_4Ser$ (SEQ ID NO:1) linkers.

Western Blot Analysis of IFNAR2/IFNβ Fusion Protein. In order to establish that the Interfusion proteins were being expressed at the appropriate molecular weight and that no free IFNβ was being expressed, supernatants from transfected cells were analyzed by Western blotting using an anti-IFNβ antibody to detect the Interfusion. The results of this analysis are shown in FIG. 13.

15 μl of culture supernatants from CHO cells transiently transfected with IFNAR2/IFNβ construct (lanes 1–6) or IFNAR2 construct (lane 7), culture medium (lane 8) or IFNβ (lane 9) were subjected to SDS-PAGE under non-reducing condition followed by electrotransfer to PVDF membrane. The membrane was probed with rabbit anti-IFNβ antibody and developed with alkaline phosphatase conjugated goat anti-rabbit using a Western-Star luminescence detection kit.

No free IFNβ was detected in the supernatants of any of the Interfusion constructs. Likewise each of the constructs expressed a protein that by Western blot was the appropriate MW for each Interfusion construct.

Example 10

Figure 14:
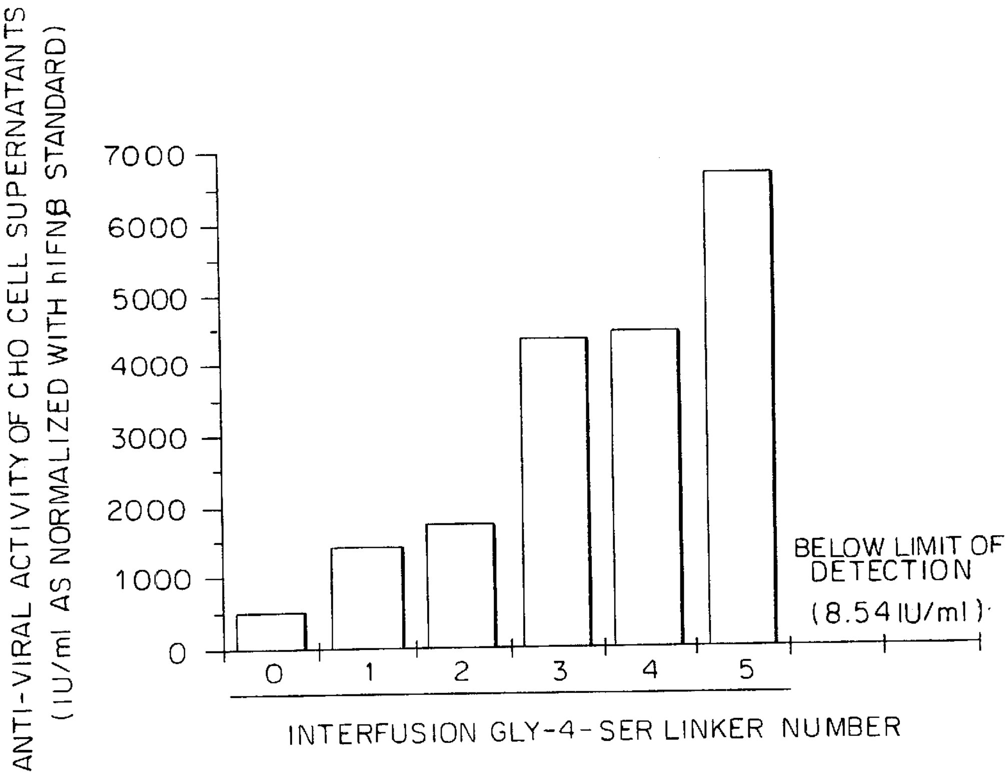
FIG. 14 is a graph showing anti-viral activity of Interfusion molecules expressed in CHO cells supernatants and normalized to IFNβ standard activity.

Anti-viral Activity of Interfusion Molecules. Each Interfusion containing culture supernatant was tested for antiviral activity in a cytopathicity assay in which WISH cells (human amniotic cells) were exposed to VSV following the addition of either IFNβ (control) or the Interfusions. The results are shown in FIG. 14.

CHO cell supernatants containing expressed recombinant proteins (as detected by ELISA and Western Blot), or CHO culture medium alone, were added in duplicate to the top row of 96-well flat-bottom tissue culture plates in a volume of 75 μl/well. 50 μl of WISH cell assay medium was added to the remaining wells of the plate. Three-fold serial dilutions of each sample were performed by removing 25 μl from the wells containing the supernatants (top row) and adding this to the next row containing the 50 μl of the WISH assay medium. In the positive control wells, the supernatant in the top row was replaced with WISH assay medium containing 1000 IU/ml human IFNβ, which was likewise serially diluted three-fold down the length of the plate. Each well then received 50 μl of a WISH cell suspension ($0.6\times10^6$ cells/ml in WISH assay medium) so that the final concentration in the top row containing REBIF® is 500 IU/ml, and the starting dilution for the CHO cell supernatants is 1:2. Following 24 hours of incubation in 5% $CO_2$ at 37° C., each well (except those designated as the uninfected control wells) received 50 μl of WISH assay medium containing vesicular stomatitis virus (1:10 of the stock). Viability of the WISH cells was determined, following an additional 48 hours of culture, by MTT conversion.

Anti-viral activity mediated by the Interfusion molecules was determined by normalizing the dilutional factor of the supernatants necessary to achieve the $EC_{50}$ to the $EC_{50}$ determined for the purified human IFNα standard. As the linker length increases, so too does the anti-viral activity of the Interfusion constructs.

Example 11

This example is a pharmacokinetic study of human IFNβ/sIFNAR2 complex in the mouse upon intravenous administration. Comparisons are performed between preformed and separately injected complex components. Thirty-six D2F1 strain mice (6–8 wks) (approximately 20 g each) are separated into four groups as follows:

Group 1 contains nine mice to be injected intravenously with a single bolus of 200 μl of a solution of 50,000 IU/ml human IFNβ (final dose of 10,000 IU/mouse).

Group 2 (nine mice) received 200 μl of a solution of 50,00 IU/ml human IFNβ and 125 mg/ml sIFNAR2 (2.5 ng/IU ratio).

Group 3 (nine mice) received (1) 200 μl of a solution of 125 mg/ml, followed by (2) 200 ml of a solution of 50,000 IU/ml human IFNβ (2.5 ng/IU ratio).

Group 4 (9 mice) received (1) 200 μl of a solution of 625 mg/ml, followed by (2) 200 ml of a solution of 50,000 IU/ml human IFNβ (10 ng/IU ratio).

Blood samples (approximately 200 μl/sample) are collected at the specified times by disruption of the retro-orbital venous plexus with a capillary tube. Three mice of each group have blood samples taken at 0.05, 2 and 12 hours post administration. Three mice of each group have blood samples taken at 0.54 and 24 hours post administration and three of each group have blood samples taken at 1, 8 and 48 hours post administration. Blood samples were allowed to clot at one hour at room temperature rimmed and microcentrifuged. Sera removed therefrom were stored at −70° C. until all samples were collected. Sera are assayed for the presence of human IFNβ by means of IFNβ specific ELISA using the Toray human IFNβ ELISA kit (TFB, Inc.) and were assayed for bioactivity using the WISH antiviral assay.

Figure 15A:
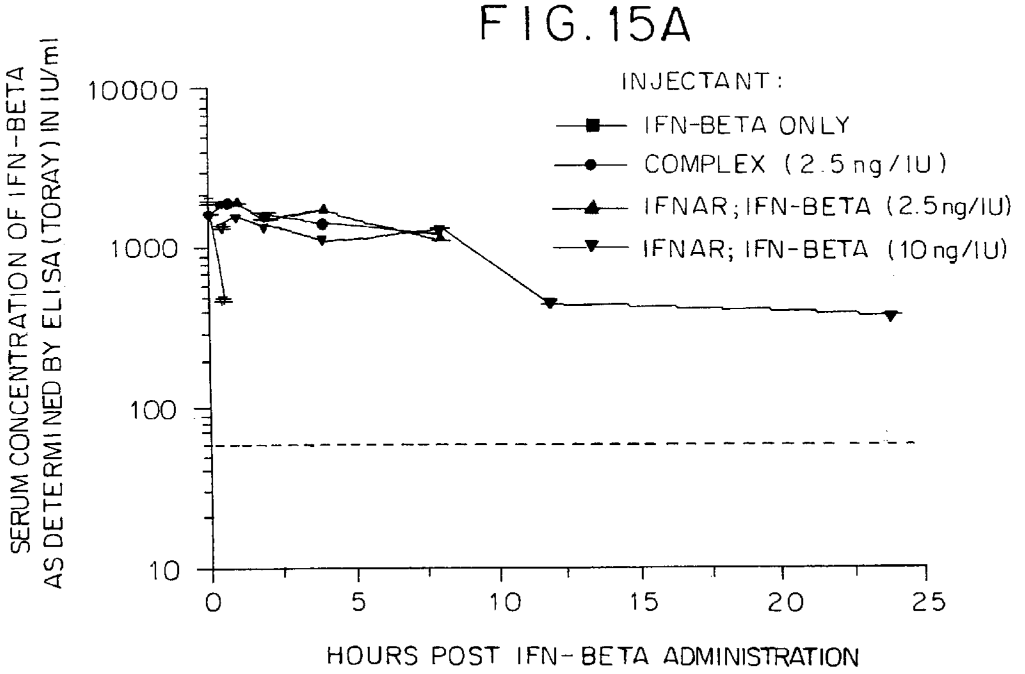
FIGS. 15A–B are graphs showing the pharmacokinetics of IFNα administered after intravenous injection of IFNAR2. IFNβ was injected either alone, as an IFNAR complex, or immediately following a separate I.V. injection of sIFNAR2. The serum half life was assessed at the indicated times post injection by IFNβ specific ELISA (FIG. 15A) and by bioactivity in the WISH antiviral assay (FIG. 15B).
Figure 15B:
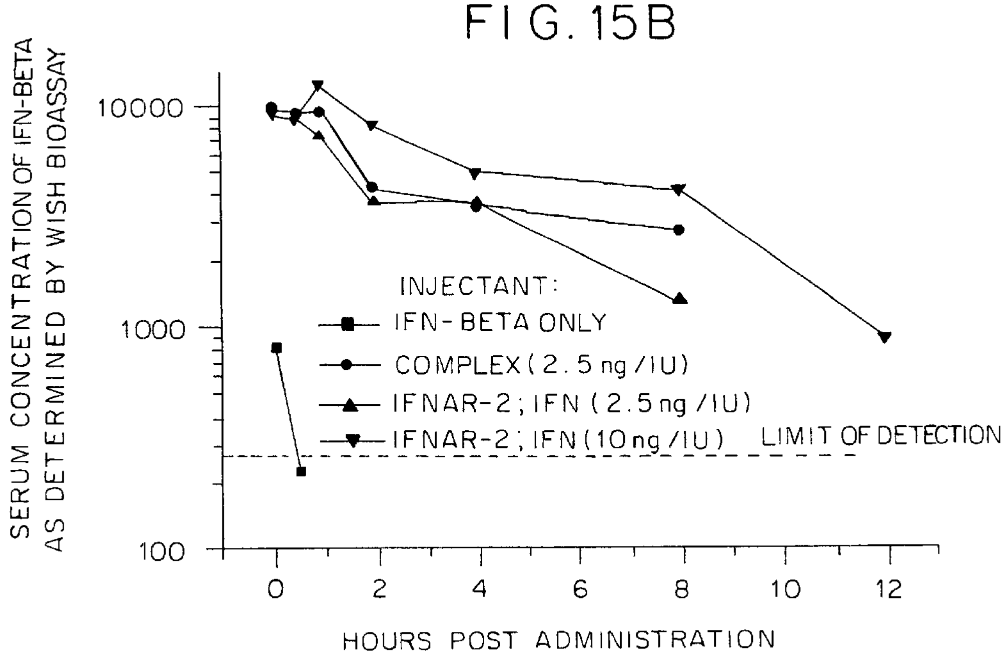

The results of the IFNβ specific ELISA assay are shown in FIG. 15A and the results of the WISH antiviral assay are shown in FIG. 15B.

It can be seen that the serum half life of IFNβ injected as IFNAR2 complex is similar to that of IFNβ injected following separate IFNAR injection. These results are consistent with an in vivo formation of an IFNβ/IFNAR2 complex with enhanced half life.

Example 12

Figure 16:
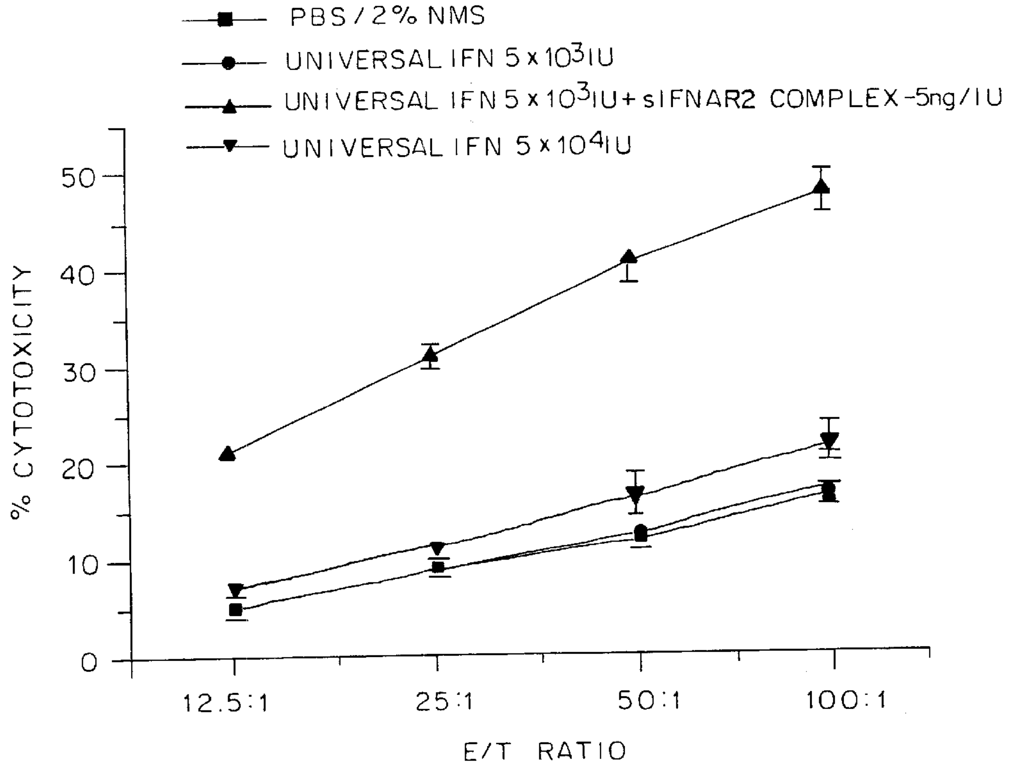
FIG. 16 is a graph showing the protective effect in terms of percent cytotoxicity of various doses of a complex of "Universal" IFN (human IFNαA/D) in a complex with sIFNAR2, as compared to administration of Universal IFN alone or a control.

C57BL/6 mice were treated with a complex of "Universal" IFN (human IFNαA/D) and sIFNAR2. The protective effect in terms of cytotoxicity was measured as compared with administration of various doses of Universal IFN alone or a control. The first group received $5\times10^3$ IU Universal IFN, complexed with 5/ng IU sIFNAR2. The second group received $5\times10^3$ IU Universal IFN. The third group received $5\times10^4$ IU Universal IFN and the fourth group received PBS/2% NMS. For each of these mice, NK activity was measured as cytotoxicity of splenic cells against the NK target cells YAC-1. The results are shown in FIG. 16. The NK activity was significantly greater in mice treated with the Universal IFN/sIFNAR2 complex as compared with mice treated with Universal IFN only.

Example 13

As indicated above, pharmacokinetic studies have demonstrated a dramatic enhancement in the serum half life of Type I IFNs when administered as a complex with sIFNAR2, the soluble form of the IFN receptor subunits. In vitro results suggest that physical association with IFNAR2 leads to the stabilization of normally labile IFN. In order to determine whether the enhanced PK profile and stabilizing effect of IFNAR2 cause an enhancement and prolongation of IFN mediated efficacy in vivo, a model was developed in which severe combined immunodeficient (scid/scid) mice are challenged with a lethal does of the IFN-sensitive Daudi human B cell lymphoma cell line (Ghetie, 1991; Ghetie, 1990). These mice developed paralysis between days 14–20 post tumor cell injection in association with histological evidence of diffused lymphoma. Notably, survival of these mice can be prolonged in dose dependent fashion by daily subcutaneous administration of human IFNβ. This model is being used to evaluate IFNAR2 as a potentiator of the biological activity associated with type 1 IFNs in vivo.

In order to establish the relationship between the mean time to paralysis and the dose of IFNβ in the Daudi scid model, five groups of 5 BALB/cByJSmn-scid/scid strain mice, 4–5 wks of age, female, received a subcutaneous administration of 200 μl per mouse per day of human IFNβ every day from day 0 to day 30. The standard Daudi cell dose, expanded from frozen stock, was $5\times10^6$ cells per mouse by subcutaneous injection in the scruff of the neck on day 0 in PBS. The groups of mice received the following amounts of IFN.

Group 1: $135\times10^4$ IU/mouse ($675\times10^4$ IU/ml).

Group 2: $45\times10^4$ IU/mouse ($225\times10^4$ IU/ml).

Group 3: $15\times10^4$ IU/mouse ($75\times10^4$ IU/ml).

Group 4: $5\times10^4$ IU/mouse ($25\times10^4$ IU/ml).

Group 5: PBS with 2% NMS

The time to paralysis as individual and mean values is shown in Table V.

TABLE V

| | Days to Paralysis | Mean (± SD) |
|---|---|---|
| Group 1 | 26, 31, 35, 37, 40 | 33.8 (5.4) |
| Group 2 | 20, 23, 23, 23, 26 | 23.0 (2.1) |
| Group 3 | 20, 20, 22, 22, 23 | 21.4 (1.3) |
| Group 4 | 17, 18, 18, 18, 18 | 17.8 (0.5) |
| Group 5 | 14, 14, 15, 15, 15 | 14.6 (0.6) |

It can thus be seen that the mean time to paralysis in the Daudi/scid xenograft model is prolonged by daily subcutaneous administration of human IFNβ in a dose dependent manner.

Example 14

In order to determine whether the antitumor effect of IFNβ can be enhanced by complexing with IFNAR2 at 2.5 ng/IU, seven groups of five mice were treated by the same protocol discussed in Example 13, except that the test materials administered to each of the groups was as follows:

| IFNβ only/mouse | IFNβ plus sIFNAR2/mouse |
|---|---|
| Group 1 $2 \times 10^2$ IU | Group 4 $2 \times 10^2$ IU plus 0.5 μg |
| Group 2 $2 \times 10^3$ IU | Group 5 $2 \times 10^3$ IU plus 5.0 μg |
| Group 3 $2 \times 10^4$ IU | Group 6 $2 \times 10^4$ IU plus 50.0 μg |
| Group 7 received Daudi cells, treament is dilluent only | |

The time to paralysis as individual and mean values is shown in the following table:

TABLE VI

| | Days to Paralysis | Mean (± SD) |
|---|---|---|
| Group 1 | 16, 16, 17, 18, 19 | 17.2 (1.3) |
| Group 2 | 17, 18, 18, 19, 19 | 18.2 (0.8) |
| Group 3 | 17, 17, 17, 18, 18 | 17.6 (0.9) |
| Group 4 | 17, 17, 18, 18, 19 | 17.8 (0.8) |
| Group 5 | 17, 18, 19, 20, 20 | 18.8 (1.3) |
| Group 6 | 21, 22, 22, 23, 26 | 22.8 (1.9)* |
| Group 7 | 16, 16, 17, 17, 17 | 16.6 (0.6) |

*Significantly different (p value ≦ 0.05) than same concentration of IFNβ in non-complexed form in pairwise group comparison as determined by one-way ANOVA.

It can be seen that the anti-tumor activity of a low dose of IFNβ $2\times10^4$ IU/mouse/day and the Daudi/scid xenograft model is significantly enhanced by complexing with IFNAR2.

In an additional experiment (not shown) the effect of injection frequency on mean paralysis time was studied. It was determined that significantly enhanced antitumor activity in the Daudi/scid xenograft model can be obtained by treatment with IFNβ/IFNAR G2 complex when injected as infrequently as once per week, as compared with free IFNβ injected as often as once per day. Furthermore, in an additional experiment (not shown) the optimum ratio of IFNAR to IFNβ was tested. It was found that the optimum ratio of IFNAR2:IFNβ in the enhancement of antitumor activity in a single concentration of IFNβ ($2\times10^4$/IU/mouse/day) was 2.5 ng IFNAR2 per pg IFNβ.

In a second experiment, it was found that the optimum ratio if IFNAR2:IFNβ in the enhancement of antitumor activity at a concentration of IFNβ $5\times10^4$ IU/mouse/day was 0.3 ng IFNAR2 per pg IFNβ. These two experiments indicate that the optimum ratio depends on the concentration of IFNα and seems to indicate that the higher the concentration of IFNβ, the lower the ratio needs to be.

In another experiment using the same model, it was established that administration of IFNAR2 alone does not enhance survival of the mice in the study.

Example 15

This example is a pharmacokinetic study to determine the serum half life of the Interfusion 5GS molecule in mouse serum following a single bolus intravenous injection. Twenty-one female B6D2F1 strain mice (6–8 wks) (approximately 20 g each) were separated into three groups as follows:

Group 1: contains nine mice injected intravenously with a single bolus of 200 μl of a solution of 100,000 IU/ml Interfusion 5GS (final dose of 20,000 IU/mouse or $5\times10^6$ IU/kg).

Group 2: (nine mice) received 200 μl of a solution of 100,000 IU/ml human IFNβ.

Group 3: contains three uninjected mice which serve as a negative control.

Assuming a blood volume of approximately 2 ml/mouse, the theoretical $C_{max}$ and $T_{max}$ is 10,000 IU/ml for Groups 1 and 2. Three mice of each of Groups 1 and 2 had blood sampled at 0.05, 2 and 12 hours post administration. Three mice of each of Groups 1 and 2 had blood sampled at 0.5, 4 and 24 hours post administration, and three mice of each of Groups 1 and 2 had blood sampled at 1, 8 and 48 hours post administration. Sera were assayed for the presence of bioactive human IFNβ using the WISH assay.

Figure 17:
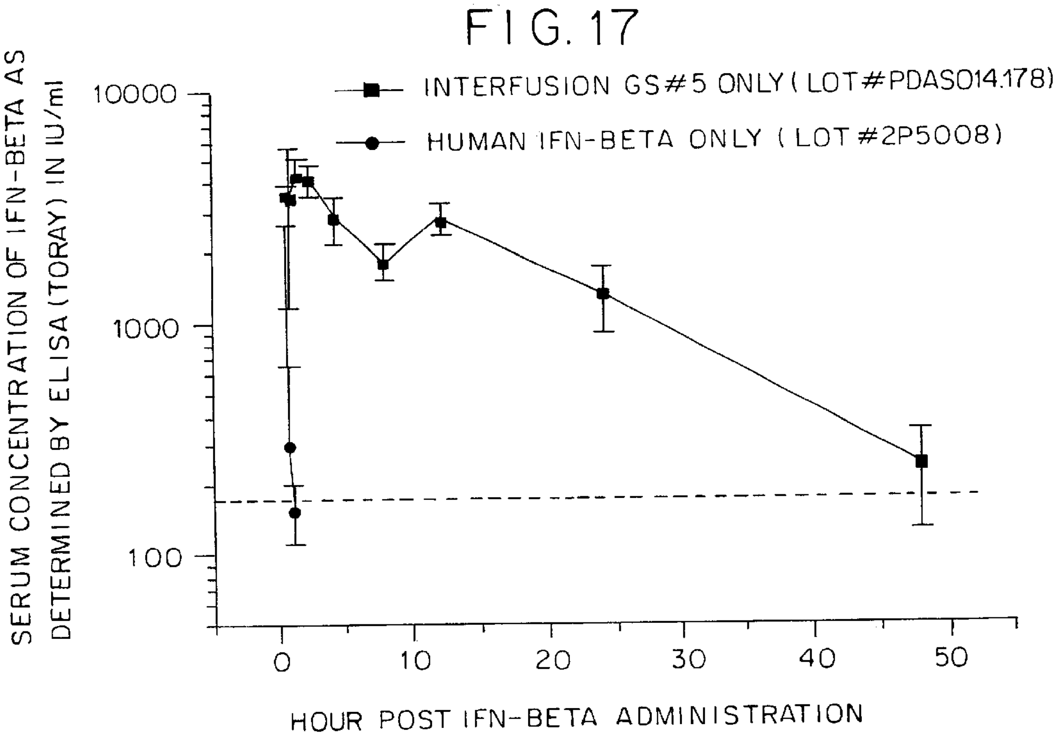
FIG. 17 is a graph showing the serum concentration of IFNβ as a function of time after a single bolus intravenous injection of either Interfusion GS5 or hIFNβ alone.

The results are shown in FIG. 17. While IFNβ is cleared almost immediately, the Interfusion molecule remains in the serum for long after injection. This shows that the fusion protein has the desired stabilizing effect.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

REFERENCES

Alam et al, "Comparative pharmacokinetics and Pharmacodynamics of two recombinant human interferon beta-1 (IFNβ-1α) products administered intramuscularly in healthy male and female volunteers", *Pharmaceutical Research* 14:546–549 (1997)

Anfinsen, "Principles That Govern The Folding of Protein Chains", *Science* 181:223–230 (1973)

Ausubel et al, *Current Protocols in Molecular Biology,* Greene Publications and Wiley Interscience (New York, 1987–1992)

Baron et al, "The interferons: A biological system with therapeutic potential in viral infections", *Antiviral Res.* 24:97–110 (1994)

Baron, et al, "The interferons. Mechanisms of action and clinical applications", *J. Am. Med. Assoc.* 266:1375–1383 (1991)

Chomczynski et al, *Anal. Biochem.* 162:156–159 (1987)

Christofinis, G. J., "Interferon Production by Human Lymphoblastoid Cell Lines of Different Origins", *Journal of General Virology* 52:169–171 (1981)

Church et al, *Proc. Natl. Acad. Sci. USA* 81:1991–1995 (1984)

Colamonici et al, "Multichain structure of the interferon alpha receptor on hematopoietic cells", *J. Immunol.* 148:2126–2132 (1992)

Colamonici et al, "Identification of a novel subunit of the Type I interferon receptor localized to human chromosome 21", *J. Biol. Chem.* 268:10895–10899 (1993)

Curtis, B. M., "Enhanced Hematopoietic Activity of a Human Granulocyte/Macrophage Colony-stimulating Factor-Interleukin 3 Fusion Protein", *Proc. Natl. Acad. Sci.* 88:5809–5813 (1991)

Domanski et al, "Cloning and Expression of a Long Form of the β Subunit of the Interferon a β Receptor That is required for Signaling", *The Journal of Biological Chemistry* 270:6 (1995)

Duncan et al, "The transcription factor interferon regulatory factor-1 is essential for natural killer cell function in vivo", *J. Exp. Med.* 184:2043–2048 (1996)

Dron et al, "Interferon α/β gene structure and regulation" in *Interferon Principles and Medical Applications,* Baron et al, Editors, (University of Texas Medical Branch: Galveston, Tex., 1992) pp. 33–45

Edington, S. M., "Biotech Products as Drug Leads", *Bio-Technology* 13:649 (1995)

Ertel et al, *Arch. Surg.* 129:1 (1994)

Fierlbeck et al, "Pharmacodynamics of recombinant IFNβ during long-term treatment of malignant melanoma", *Journal of Interferon and Cytokine Research* 16:777 (1996)

Ghetie et al, *Cancer Research* 51:5876 (1991)

Ghetie et al, *Blood* 80:2315 (1990)

Graff et al, *Mol Cell. Biol.* 2:93–96 (1982)

Grantham, *Science* 185:X62–X64 (1974)

Grazia Cusi, M., "Harlequin Granulocyte-colony Stimulating Factor Interleukin 6 Molecules with Bifunctional and Antagonistic Activities", *Immunotechnology* 3:61–69 (1997)

Ibanez, C. F., "Chimeric Molecules with Multiple Neurotrophic Activities Reveal Structural Elements Determining the Specificities of NGF and BDNF", *EMBO Journal* 10:2105–2110 (1991)

Kazam et al, *J. Biol. Chem.* 270:1 (1995)

Keown, W. A., "Methods for Introducing DNA into Mammalian Cells", *Methods in Enzymology* 185:527–537 (1990)

Lengyl, P., "Biochemistry of interferons and their actions", *Ann. Rev. Biochem.* 51:251–282 (1982)

Lutfalla et al, "Mutant U5A cells are complemented by an interferon-α/β receptor subunit generated by alternative processing of a new member of a cytokine receptor gene cluster", *EMBO Journal* 14:5100–5108 (1995)

Meinkoth et al, *Anal. Biochem.* 138:267–284 (1984)

Nagai et al, *Nature* 309:810 (1984)

Novick et al, *J. Immunol.* 129:2244–2247 (1982)

Novick et al, "Soluble interferon-alpha receptor molecules are present in body fluids" *FEBS Lett.* 314:445–448 (1992)

Novick et al, "The human interferon α/β receptor: Characterization and molecular cloning", *Cell* 77:391–400 (1994)

Novick et al, "Soluble and membrane-anchored forms of the human IFN-α/β receptor", *J. Leuk. Bio.* 57:712–718 (1995)

Olins, P. O., "Recent Advances in Heterologous Gene Expression in Escherichia coli", *Current Opinion in Biotechnology* 4:520–525 (1993)

Pestka, et al, "Interferons and their actions", *Ann. Rev. Biochem.* 56:727–777 (1987)

Platanias et al, "Characterization of the α-subunit of the interferon α receptor: evidence of N- and O-linked glycosylation and association with other surface proteins", *J. Immunol.* 150:3382–3388 (1993)

Platanias et al, "Tyrosine phosphorylation of the α and β subunits of the Type I interferon receptor" *J. Biol. Chem.* 269:17761–17764 (1994)

Platanias et al, "Differences in interferon α and β signaling," *J. Biol. Chem.* 271:23630–23633 (1996)

Qureshi et al, "Function of Stat2 protein in transcriptional activation by alpha interferon", *Mol. Cell. Bio.* 16:288–293 (1996)

Ratner, M., "Protein Expression in Yeast", *Bio/Technology* 7:1129–1133 (1989)

Reff, M., "High-level Production of Recombinant Immunoglobulins in mammalian Cells", *Current Opinion in Biotechnoloqy* 4:573–576 (1993)

Reuveny, S., "Production of Recombinant Proteins in High Density Insect Cell Cultures", *Biotechnology and Bioengineering* 42:235–239 (1993)

Salmon et al, "Pharmacokinetics and phamacodynamics of recombinant human IFNβ in healthy male volunteers", *Journal of Interferon and Cytokine Research* 16:759 (1996)

Sambrook et al, *Molecular Cloning: A Laboratory Manual,* 2nd Ed., Cold Spring Harbor Press (Cold Spring Harbor, N.Y., 1989)

Sharf et al, "Functional domain analysis of interferon consensus sequence binding protein (ICSBP) and its association with interferon regulatory factors," *J. Biol. Chem.* 270:13063–13069 (1995)

Smith, G. E., "Production of Human Beta Interferon in Insect Cells Infected with a Baculovirus Expression Vector", *Molecular and Cellular Biology* 3:2156–2165 (1983)

Szilagyi et al, *Biochim. Biophys. Acta* 1251:1 (1995)

Tan et al, "The linkage of genes for the human interferon induced antiviral protein and indophenol oxidase-B traits to chromosome G-21", *J. Exp. Med.* 137:317–330 (1973)

Terlizzese, M., "In vitro comparison of inhibiting ability of soluble TNF receptor p75 (TBPII) vs. Soluble TNF Receptor p55 (TBPI) against TNF-α and TNF-β", *Journal of Interferon and Cytokine Research* 16:1047–1053 (1996)

Urlaub et al, *Proc. Natl. Acad. Sci USA* 77:4216–4220 (1980)

Utsumi, J., "Characterization of E.coli-derived Recombinant Human Interferon-beta as Compared with Fibroblast Human Interferon-beta", *Journal of Biochemistry* 101:1199–1208 (1987)

Uze et al, "Genetic transfer of a functional human interferon alpha receptor into mouse cells: cloning and expression of its cDNA", *Cell* 60:225–234 (1990)

Weissmann et al, "The interferon genes", *Prog. Nucleic Acid Res.* 33:251–302 (1986)

Yan et al, "Molecular characterization of an alpha interferon receptor 1 subunit (IFNaR1) domain required for TYK2 binding and signal transduction", *Mol. Cell. Bio.* 16:2074–2082 (1996)

Yang et al, "Direct association of STAT3 with the IFNAR-1 chain of the human Type I interferon receptor", *J. Biol. Chem.* 271:8057–8061 (1996)

What is claimed is:

1. A method for prolonging the in vivo effect of Type I interferon (IFN), comprising:

administering to a patient in need of Type I IFN therapy a complex of Type I IFN and a subunit of the human interferon α/β receptor (IFNAR) which is capable of binding to the Type I IFN of the complex, in an amount effective to provide such IFN therapy, wherein said Type I IFN has a sequence consisting essentially of the sequence of a) a native Type I IFN;

b) a fragment of a) which has Type I IFN receptor agonist or antagonist activity;

c) a variant of a) or b) which has at least 70% sequence identity with a) or b) and which has Type I IFN receptor agonist or antagonist activity; or d) a variant of a) or b) which is encoded by a DNA sequence which hybridizes to the complement of the native DNA sequence encoding a) or b) under moderately stringent conditions and which has Type I IFN receptor agonist or antagonist activity;

or a salt or functional derivative of a), b), c), or d) which has Type I IFN receptor agonist or antagonist activity; and wherein said IFNAR has a sequence consisting essentially of the sequence of e) a native human IFNAR polypeptide chain;

f) a fragment of e) which has IFNAR receptor agonist or antagonist activity;

g) a variant of e) or f) which has at least 70% sequence identity with e) or f) and which has IFNAR receptor agonist or antagonist activity;

h) a variant of e) or f) which is encoded by a DNA sequence which hybridizes to the complement of the native DNA sequence encoding e) or f) under moderately stringent conditions and which has IFNAR biological activity;

or a salt or functional derivative of e), f), g), or h) which has IFNAR biological activity, with the proviso that when said Type I IFN and said IFNAR are administered separately and said complex is formed in vivo, the amount of IFNAR administered is an amount effective to prolong the in vivo effect of the Type I IFN.

2. A method in accordance with claim 1, wherein said complex comprises a non-covalent complex of said Type I IFN and said IFNAR.

3. A method in accordance with claim 2, wherein said Type I IFN and said IFNAR are administered separately and said complex is formed in vivo.

4. A method in accordance with claim 1, wherein said complex comprises a complex in which said Type I IFN is bound to said IFNAR by a covalent bond.

5. A method in accordance with claim 1, wherein said complex comprises a fusion protein in which said Type I IFN is bound to said IFNAR by a peptide bond.

6. A method in accordance with claim 5, wherein said Type 1 IFN is linked to said IFNAR by means of a peptide linker.

7. A method in accordance with claim 1, wherein said Type I IFN is an IFNα, an IFNβ, or an IFNω.

8. A method in accordance with claim 7, wherein said Type I IFN is IFNβ.

9. A method in accordance with claim 1, wherein said IFNAR is the beta subunit of the human interferon α/β receptor (IFNAR2).

10. A method in accordance with claim 1, wherein said native human IFNAR polypeptide chain of e) is the extracellular domain of a native human IFNAR polypeptide chain.

11. A method in accordance with claim 3, wherein said native human IFNAR polypeptide chain of e) is the extracellular domain of a native human IFNAR polypeptide chain.

12. A method for potentiating the biological effects of Type I interferon (IFN), comprising:

administering to a patient in need of Type I IFN therapy a subunit of the human interferon α/β receptor (IFNAR) which is capable of binding to the Type I IFN to be potentiated, in an amount effective to provide such IFN therapy, wherein said IFNAR has a sequence consisting essentially of the sequence of a) a native human IFNAR polypeptide chain;

b) a fragment of a) which has IFNAR receptor agonist or antagonist activity;

c) a variant of a) or b) which has at least 70% sequence identity with a) or b) and which has IFNAR receptor agonist or antagonist activity; or d) a variant of a) or b) which is encoded by a DNA sequence which hybridizes to the complement of the native DNA sequence encoding a) or b) under moderately stringent conditions and which has Type I IFN receptor agonist or antagonist activity;

or a salt or functional derivative of a), b), c), or d) which has IFNAR receptor agonist or antagonist activity.

13. An isolated molecule comprising a complex of a Type I interferon (IFN) and a subunit of the human interferon α/β receptor (IFNAR) which is capable of binding to the Type I IFN of the complex, in which said Type I IFN is bound to said IFNAR by a covalent bond or a peptide bond, wherein said Type I IFN has a sequence consisting essentially of the sequence of a) a native Type I IFN;

b) a fragment of a) which has Type I IFN receptor agonist or antagonist activity;

c) a variant of a) or b) which has at least 70% sequence identity with a) or b) and which has Type I IFN receptor agonist or antagonist activity; or d) a variant of a) or b) which is encoded by a DNA sequence which hybridizes to the complement of the native DNA sequence encoding a) or b) under moderately stringent conditions and which has Type I IFN receptor agonist or antagonist activity;

or a functional derivative of a), b), c), or d) which has Type I IFN receptor agonist or antagonist activity; and wherein said IFNAR has a sequence consisting essentially of the sequence of e) a native human IFNAR polypeptide chain;

f) a fragment of e) which has IFNAR biological activity;

g) a variant of e) or f) which has at least 70% sequence identity with e) or f) and which has IFNAR biological activity; or h) a variant of e) or f) which is encoded by a DNA sequence which hybridizes to the complement of the native DNA sequence encoding e) or f) under moderately stringent conditions and which has IFNAR biological activity;

or a salt or functional derivative of e), f), g), or h) which has IFNAR biological activity.

14. A molecule in accordance with claim 13, wherein said Type I IFN is bound to said IFNAR by a covalent bond.

15. A molecule in accordance with claim 13, wherein said Type I IFN is bound to said IFNAR by a peptide bond.

16. A molecule in accordance with claim 15, wherein said Type 1 IFN is linked to said IFNAR by means of a peptide linker.

17. A molecule in accordance with claim 16, wherein said peptide linker is (GGGGS)n (SEQ ID NO:1) wherein n=1–5.

18. A molecule in accordance with claim 13, wherein said Type I IFN is an IFNα, an IFNβ, or an IFNω.

19. A molecule in accordance with claim 18, wherein said Type I IFN is IFNβ.

20. A molecule in accordance with claim 13, wherein said IFNAR is the beta subunit of the human interferon α/β receptor (IFNAR2).

21. A molecule in accordance with claim 13, wherein said native human IFNAR polypeptide chain of e) is the extracellular domain of a native human IFNAR polypeptide chain.

22. A DNA encoding a fusion protein which is a molecule in accordance with claim 15.

23. A host cell transformed with a vector carrying a DNA in accordance with claim 22 in a manner which permits expression of said fusion protein.

24. A method of making a fusion protein comprising culturing a host cell in accordance with claim 23 and recovering the fusion protein expressed thereby.

25. A method for improving the shelf life of Type I interferon, comprising storing said interferon in the form of a complex in accordance with claim 10 or a complex in which said IFN is bound to said IFNAR by a non-covalent bond in a pharmaceutically acceptable formulation.

26. A method in accordance with claim 25, wherein the pharmaceutically acceptable formulation is non-acidic.

27. A pharmaceutical composition consisting essentially of a pharmaceutically acceptable carrier and a complex of a Type I interferon (IFN) and a subunit of the human interferon α/α receptor (IFNAR) which is capable of binding to the type I IFN of the complex, wherein said Type I IFN has a sequence consisting essentially of the sequence of a) a native Type I IFN;

b) a fragment of a) which has Type I IFN receptor agonist or antagonist activity;

c) a variant of a) or b) which has at least 70% sequence identity with a) or b) and which has Type I IFN receptor agonist or antagonist activity; or d) a variant of a) or b) which is encoded by a DNA sequence which hybridizes to the complement of the native DNA sequence encoding a) or b) under moderately stringent conditions and which has Type I IFN receptor agonist or antagonist activity;

or a salt or functional derivative of a), b), c), or d) which has Type I IFN receptor agonist or antagonist activity; and wherein said IFNAR has a sequence consisting essentially of the sequence of e) a native human IFNAR polypeptide chain;

f) a fragment of e) which has IFNAR receptor agonist or antagonist activity;

g) a variant of e) or f) which has at least 70% sequence identity with e) or f) and which has IFNAR receptor agonist or antagonist activity; or h) a variant of e) or f) which is encoded by a DNA sequence which hybridizes to the complement of the native DNA sequence encoding e) or f) under moderately stringent conditions and which has IFNAR receptor agonist or antagonist activity;

or a salt or functional derivative of e), f), g), or h) which has IFNAR biological activity.

28. A pharmaceutical composition in accordance wi th claim 27, wherein said native human IFNAR polyeptide chain of e) is the extracellular domain of a native human IFNAR polypeptide chain.

* * * * *